(12) United States Patent
Goetz

(10) Patent No.: US 11,813,038 B2
(45) Date of Patent: *Nov. 14, 2023

(54) REMOTE TITRATION OF THERAPY DELIVERED BY AN IMPLANTABLE MEDICAL DEVICE

(71) Applicant: Medtronic, Inc., Minneapolis, MN (US)

(72) Inventor: Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 594 days.

This patent is subject to a terminal disclaimer.

(21) Appl. No.: 17/025,518

(22) Filed: Sep. 18, 2020

(65) Prior Publication Data

US 2021/0000349 A1 Jan. 7, 2021

Related U.S. Application Data

(63) Continuation of application No. 14/137,673, filed on Dec. 20, 2013, now Pat. No. 10,806,344, which is a
(Continued)

(51) Int. Cl.
*A61N 1/00* (2006.01)
*A61B 5/00* (2006.01)
(Continued)

(52) U.S. Cl.
CPC ......... *A61B 5/0031* (2013.01); *A61M 5/1723* (2013.01); *A61N 1/36007* (2013.01);
(Continued)

(58) Field of Classification Search
CPC ............... A61B 5/0031; A61M 5/1723; A61N 1/36007; A61N 1/36071; A61N 1/37252; A61N 1/37282

See application file for complete search history.

(56) References Cited

U.S. PATENT DOCUMENTS 6,044,297 A * 3/2000 Sheldon ............. A61N 1/36542
600/585
6,662,052 B1 12/2003 Sarwal et al.
(Continued)

FOREIGN PATENT DOCUMENTS

EP 1491234 A1 12/2004
WO 9622125 A1 7/1996
(Continued)

OTHER PUBLICATIONS

Prosecution History from U.S. Pat. No. 8,615,299 dated Apr. 14, 2010 through Aug. 20, 2013, 76 pp.
(Continued)

*Primary Examiner* — Scott M. Getzow
(74) *Attorney, Agent, or Firm* — Shumaker & Sieffert, P.A.

(57) ABSTRACT

Techniques for remotely titrating a therapy delivered using an implantable medical device system are disclosed. An implantable medical device delivers therapy according to a first program. The system collects patient data relating to at least one of an efficacy of, or side effects resulting from, the delivered therapy, and transmits the patient data to a remote network device. A clinician may then analyze the patient data and determine if changes to the therapy are warranted. The clinician may then transmit a programming change, e.g., a modification to the first program or a new, second program, to the implantable medical device system, and the implantable medical device may deliver therapy according to the changed programming. The process of receiving patient data and modifying the therapy programming may be repeated multiple times until the therapy is adequately titrated, e.g., until the patient data indicates adequate efficacy and/or acceptable side effects.

18 Claims, 16 Drawing Sheets

Related U.S. Application Data continuation of application No. 12/682,996, filed as application No. PCT/US2008/078099 on Sep. 29, 2008, now Pat. No. 8,615,299.

(60) Provisional application No. 61/000,160, filed on Oct. 24, 2007.

(51) Int. Cl.
- *A61N 1/372* (2006.01)
- *A61M 5/172* (2006.01)
- *A61N 1/36* (2006.01)

(52) U.S. Cl.
CPC ..... *A61N 1/36071* (2013.01); *A61N 1/37252* (2013.01); *A61N 1/37282* (2013.01)

(56) References Cited

U.S. PATENT DOCUMENTS

| | | |
|---|---|---|
| 8,615,299 B2 | 12/2013 | Goetz |
| 2001/0031997 A1 | 10/2001 | Lee |
| 2001/0034542 A1 | 10/2001 | Mann |
| 2002/0029002 A1 | 3/2002 | Bardy |
| 2002/0143372 A1 | 10/2002 | Snell et al. |
| 2002/0183693 A1 | 12/2002 | Peterson et al. |
| 2005/0075669 A1* | 4/2005 | King ............... A61N 1/36021 424/9.2 |
| 2005/0216064 A1* | 9/2005 | Heruth ............ A61N 1/36146 607/3 |
| 2006/0089592 A1 | 4/2006 | Kadhiresan et al. |
| 2006/0190051 A1* | 8/2006 | Gerber ............. A61N 1/36007 607/41 |
| 2006/0206067 A1 | 9/2006 | Ferek-Petric |
| 2006/0235289 A1 | 10/2006 | Wesselink et al. |
| 2007/0060797 A1 | 3/2007 | Ball et al. |
| 2007/0142868 A1 | 6/2007 | Moon et al. |
| 2007/0150019 A1 | 6/2007 | Youker et al. |
| 2008/0088436 A1 | 4/2008 | Reeves et al. |
| 2012/0136410 A1 | 5/2012 | Rezai et al. |
| 2014/0107567 A1 | 4/2014 | Goetz |

FOREIGN PATENT DOCUMENTS

| | | |
|---|---|---|
| WO | 2004067083 A2 | 8/2004 |
| WO | 2004093989 A1 | 11/2004 |
| WO | 2006099035 A1 | 9/2006 |
| WO | 2007079543 A1 | 7/2007 |
| WO | 2007112092 A2 | 10/2007 |
| WO | 2009055202 A1 | 4/2009 |
| WO | 2009055204 A1 | 4/2009 |
| WO | 2009055206 A1 | 4/2009 |
| WO | 2009055207 A2 | 4/2009 |

OTHER PUBLICATIONS

International Search Report and Written Opinion of international application No. PCT/US2008/078099, dated Dec. 11, 2008, 15 pp.
Reply to Written Opinion from international application No. PCT/US2008/078099, filed Aug. 14, 2009, 18 pp.
International Preliminary Report on Patentability from international application No. PCT/US2008/078099, dated Feb. 2, 2010, 13 pp.
International Search Report and Written Opinion of international application No. PCT/US2008/078134, dated Jun. 6, 2009, 12 pp.
Reply to Written Opinion from international application No. PCT/US2008/078134, filed Sep. 9, 2009, 11 pp.
Second Written Opinion of international application No. PCT/US2008/078134, dated Feb. 5, 2010, 10 pp.
Reply to Second Written Opinion from international application No. PCT/US2008/078134, filed Apr. 5, 2010, 13 pp.
International Preliminary Report on Patentability from international application No. PCT/US2008/078134, dated Apr. 22, 2010, 20 pp.
International Search Report and Written Opinion of international application No. PCT/US2008/078125, dated Feb. 2, 2009, 17 pp.
International Search Report and Written Opinion of international application No. PCT/US2008/078127, dated Dec. 12, 2008, 13 pp.
Reply to Written Opinion from international application No. PCT/US2008/078127, filed Jun. 12, 2009, 15 pp.
International Preliminary Report on Patentability from international application No. PCT/US2008/078127, dated Dec. 21, 2009, 11 pp.
International Search Report and Written Opinion of international application No. PCT/US2008/078114, dated Feb. 10, 2009, 12 pp.
Reply to Written Opinion from international application No. PCT/US2008/078114, filed Aug. 21, 2009, 15 pp.
International Preliminary Report on Patentability from international application No. PCT/US2008/078114, dated Dec. 18, 2009, 10 pp.
Prosecution History from U.S. Appl. No. 14/137,673, dated Jan. 4, 2016 through Jun. 25, 2020, 232 pp.

\* cited by examiner

REMOTE TITRATION OF THERAPY DELIVERED BY AN IMPLANTABLE MEDICAL DEVICE

This application is a continuation of U.S. application Ser. No. 14/137,673, which was filed on Dec. 20, 2013 and is a continuation of U.S. application Ser. No. 12/682,996, which was filed on Apr. 14, 2010 and is a U.S. National Stage filing under 35 U.S.C. § 371 of PCT Application No. PCT/US2008/78099, which was filed on Sep. 29, 2008 and claims the benefit of U.S. Provisional Application No. 61/000,160, which was filed on Oct. 24, 2007, the entire content of each of which is incorporated herein by reference in its entirety.

TECHNICAL FIELD

The invention relates to the delivery of therapy using a medical device and, more particularly, to remotely programming the delivery of therapy by the medical device.

BACKGROUND

Medical devices that deliver a therapy to a patient often do so according to a program that includes a plurality of parameters. Each of the parameters of such a program defines an aspect of the therapy as delivered by the medical device according to that program. For example, the programs used by medical devices that deliver therapy in the form of electrical stimulation, such as neurostimulators, typically include parameters that define characteristics of the electrical stimulation waveform to be delivered. Where electrical stimulation is delivered in the form of electrical pulses, for example, the parameters for such a program may include a voltage or current amplitude, a pulse width, and a rate at which the pulses are to be delivered by the medical device. Further, where a medical device that delivers electrical stimulation is implantable and, as is typical for implantable neurostimulators, coupled to an electrode set including a plurality of electrodes, such a program may include an indication of the particular electrodes within the electrode set to be used to deliver the pulses, and the polarities of the selected electrodes. As another example, the programs used by medical devices that deliver therapy via infusion of a drug or other agent may include parameters that define flow rates, agent types or concentrations, and infusion type, e.g., continuous or bolus.

In most cases, a clinician creates the one or more programs that a medical device will use to deliver therapy to a patient during an initial programming session. In the case of implantable medical devices, the initial programming session typically occurs shortly after the device is implanted in the patient. The values for each of the parameters of a program may have a significant impact on the efficacy and side effects of the delivery of therapy according to that program. The process of selecting values for the parameters that provide adequate results can be time consuming. In particular, the process may require a great deal of trial-and-error testing of numerous potential combinations of parameter values before a "best" program is discovered. A "best" program may be a program that is better in terms of clinic efficacy versus side effects experienced than other programs tested. The process is particularly burdensome in the case of programming implantable neurostimulators for delivery of spinal cord stimulation therapy, which are often coupled to an electrode set including eight or sixteen electrodes. The number of possible combinations of electrodes that could be tested during a programming session from a set of that size is substantial, e.g., potentially on the order of tens or hundreds of thousands, or even millions of possible electrode combinations.

In some cases, the clinician may test combinations of parameter values, i.e., potential programs, by manually specifying each combination to test based on intuition or some idiosyncratic methodology, and recording notes on the efficacy and side effects of each combination after delivery of stimulation according to that combination. During a programming session, the clinician may be required to make notations describing the parameters of a number of tested programs and feedback received from the patient regarding the perceived efficacy or side effects of each program. The clinician may then select one or more "best" programs based on the notations.

Even after this often-lengthy process, the programs selected during an initial programming session may ultimately prove to be inadequate. The eventual inadequacy of the initial programming may be due to a variety of problems, including progression of symptoms and/or an underlying ailment, increased or changed symptoms or side effects during activities and/or postures that were not replicated in the clinic during the initial programming session, slow onset of side effects and, in the case of delivery of stimulation via electrodes located on implantable leads, lead migration. If the programs selected during an initial programming session prove to be inadequate, the patient must return to the clinic for a follow-up programming session. Multiple follow-up programming sessions may be required over the period of time that the medical device is used to deliver therapy to the patient.

SUMMARY

In general, the current disclosure is directed to a method of remotely programming an implantable medical device (IMD) system. Titration of a therapy administered by the IMD system may be accomplished remotely based on data collected by internal or external patient sensors, and/or data input by the patient. A clinician may access the patient data via a network using a remote networking device, and determine whether programming changes are necessary to promote or maintain therapy efficacy, or reduce side-effects. The clinician may determine therapy parameter changes or new programs based on the sensor data, and transmit the programs or parameter changes from the remote networking device to the IMD system via the network. The process of receiving patient data and modifying the therapy programming may be repeated multiple times until the therapy is adequately titrated, e.g., until the sensor data indicates adequate efficacy and/or acceptable side effects.

In one embodiment, the invention includes a method comprising delivering a therapy from an implantable medical device to a patient according to at least one therapy program, generating patient data with an implantable medical device system that comprises the implantable medical device, wherein the patient data relates to at least one of an efficacy or a side effect of the therapy, transmitting the patient data from the IMD system to a remote networking device via a network, and receiving at the implantable medical device system a programming change for the therapy from the remote networking device via the network, wherein the programming change is determined at the remote networking device based on an analysis of the patient data.

In another embodiment, the invention is directed to an implantable medical device system comprising an implantable medical device that delivers a therapy to a patient according to at least one therapy program, and at least one device that generates patient data, wherein the patient data relates to at least one of an efficacy or a side effect of the therapy, transmits the patient data to a remote networking device via a network, and receives a programming change for the therapy from the remote networking device via the network, wherein the programming change is determined at the remote networking device based on an analysis of the patient data.

In another embodiment, the invention is directed to a method comprising receiving patient data from an implantable medical device system at a remote networking device via a network, wherein the implantable medical device system comprises an implantable medical device that delivers a therapy according to at least one therapy program, and the patient data relates to at least one of an efficacy or a side effect of the therapy delivered by the implantable medical device. The method further comprises analyzing the patient data at the remote networking device, determining, based on the analysis of the data, a programming change for the therapy, and transmitting the programming change to the implantable medical device system via the network.

In another embodiment, the invention is directed to a remote networking device comprising a communication module, a user interface, and a processor. The processor receives patient data from an implantable medical device system via a network and the communication module, wherein the implantable medical device system comprises an implantable medical device that delivers a therapy according to at least one therapy program, and the patient data relates to at least one of an efficacy or a side effect of the therapy delivered by the implantable medical device, presents the patient data to a user via the user interface, receives a programming change for the therapy via the user interface, and transmits the programming change to the implantable medical device system via the network and the communication module.

The invention is capable of providing one or more advantages. For example, titrating therapy over time may allow the therapy to be changed over time to address, as examples, progression of symptoms and/or an underlying ailment, increased or changed symptoms or side effects during activities and/or postures that were not replicated in the clinic during the initial programming session, slow onset of side effects, or lead migration. Furthermore, remotely titrating therapy may save patient and clinician time, and further patient and clinician convenience, by avoiding in-clinic, follow-up programming sessions.

DETAILED DESCRIPTION

Figure 1:
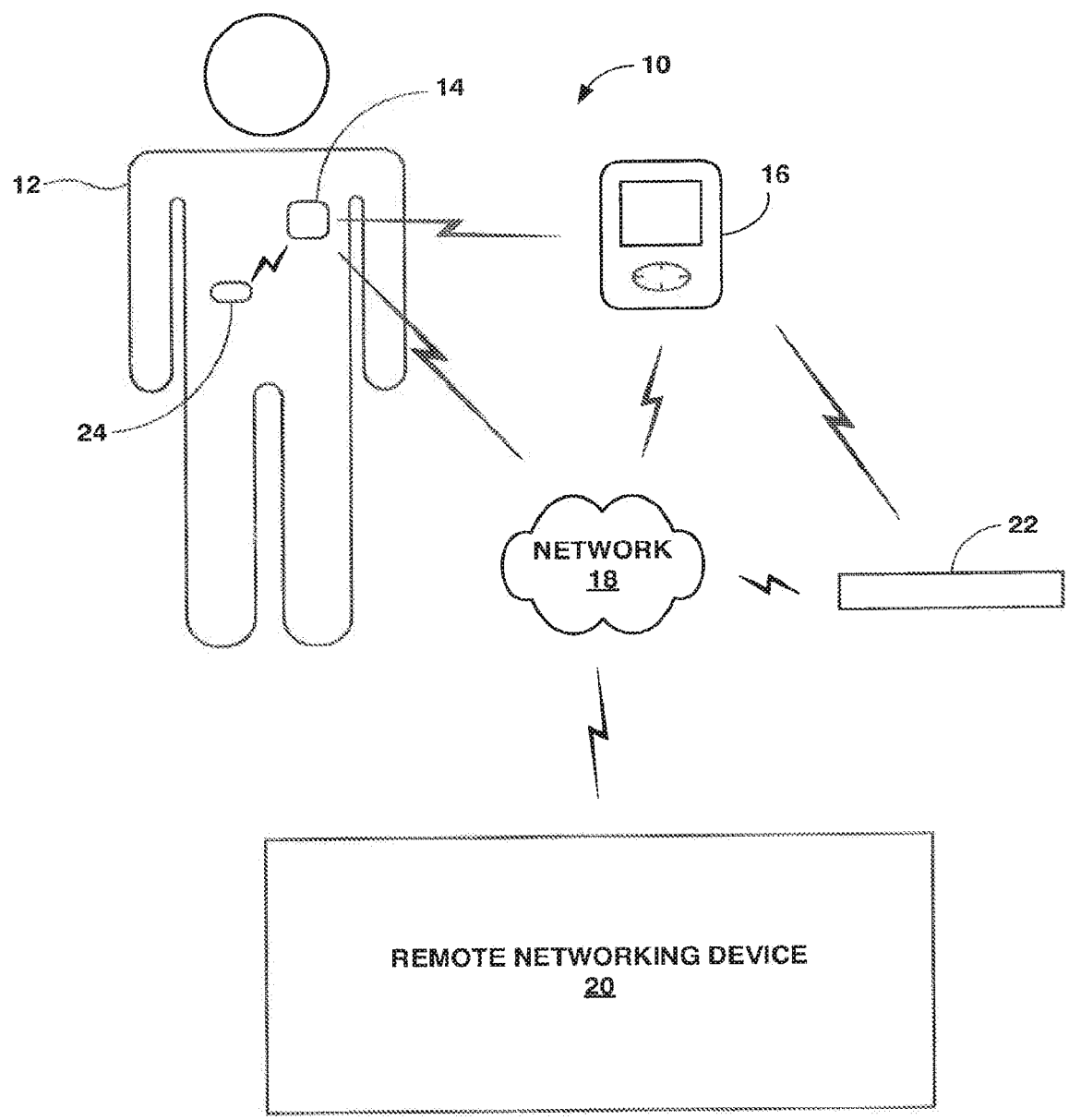
FIG. 1 is a schematic diagram illustrating an example embodiment of an IMD system that communicates with a remote networking device.

FIG. 1 is a schematic diagram illustrating an embodiment of the current invention. An implantable medical device (IMD) system 10 includes a programmer 16, internal sensor 24, and optional external sensor 22. IMD system 10 further includes IMD 14 associated with patient 12. IMD system 10 may communicate with a remote networking device 20 via a network 18.

IMD 14 delivers a therapy to patient 12. Examples of therapies that may be provided by IMD 14 include spinal cord stimulation (SCS), deep brain stimulation (DBS), neurostimulation to treat incontinence, neurostimulation to treat gastrointestinal disorders, drug delivery, or the like. Although IMD 14 is shown implanted in the chest cavity of patient 12, it shall be understood that IMD 14 may be implanted at any suitable location within patient 12, including, but not limited to, the cranium, abdomen, the lower back, or buttocks of patient 12.

IMD 14 may include or be communicatively coupled to an internal sensor 24. Internal sensor 24 may be used to collect physiological data regarding an efficacy of therapy being administered by IMD 14. Internal sensor 24 may be any sensor that senses or responds to any physiological parameter associated with the therapy provided by IMD 14. For example, internal sensor 24 may be a mechanical sensor, an electrical sensor, a chemical sensor, or it may measure temperature, auditory levels, and the like. In some embodiments, the internal sensor 24 may measure, for example, activity levels of a patient 12, glucose levels, impedance, distension of the stomach or other organs, urine flow, urine or blood pH, body temperature, bladder contraction, brain electrical activity, electroencephalogram (EEG) morphology, pulse rate, respiration rate, and the like.

External sensor 22 may also collect data regarding one or both of the efficacy of therapy being delivered by IMD 14, or side effects resulting from the therapy. Data collected by external sensor 22 may then be communicated to IMD 14, programmer 16, and/or remote networking device 20. External sensor 22 may communicate the sensor data collected by external sensor 22 over network 18. In other embodiments, external sensor 22 may communicate the sensor data to one or both of IMD 14 or programmer 16, which may in turn communicate the sensor data over network 18. In some embodiments, the external sensor is a scale, a blood glucose monitor, an accelerometer, an electrochemical sensor, a moisture sensor, and the like. In some embodiments, programmer 16 may include one or more external sensor 22.

Programmer 16 may further include a user interface comprising a display and/or an input device, such as a keypad or pointing device. In one example, a display may allow a patient to monitor his or her therapy. In some embodiments, an input device may allow the patient to initiate therapy, make changes to one or more parameters of one or more programs, or input information regarding the effects of therapy. In some embodiments, a clinician may utilize a programmer 16 to interrogate IMD 14 or make changes to the therapy parameter sets. Programmer 16 may, as illustrated in FIG. 1, take the form of a handheld computing device. However, in various embodiments, programmer 16 may be any type of computing device.

IMD 14, sensors 22, 24, and programmer 16 may wirelessly communicate using radio frequency (RF) techniques known in the art, such as RF communication according to the 802.11 or Bluetooth specification sets, or other standard or proprietary telemetry protocols. Communication between IMD 14 and programmer 16 may allow two-way transfer of information. In one example, programmer 16 transfers control data, such as sets of therapy parameters, to IMD 14. In some embodiments, IMD 14 may transmit usage information and/or physiological parameters relating to the therapy provided by IMD 14. As one example, usage information may include the number of times patient 12 has initiated therapy. As another example, physiological parameters may include those gathered by internal sensor 24 or external sensor 22.

Network 18 may facilitate communication between programmer 16, IMD 14, external sensor 22 and remote networking device 20. In this way, data may be exchanged between two or more of the apparatuses. Network 18 may, as examples, include one or more of a local area network (LAN), wide area network (WAN), public switched telephone network (PSTN), or cellular telephone network.

Remote networking device 20 may allow a clinician or another authorized user, such as a technical expert, to communicate remotely with IMD 14 or other components of system 10 via network 18. Remote networking device 20 may be any computing device with the ability to contact a network, such as a cellular telephone, personal digital assistant (PDA), tablet personal computer (PC), laptop, desktop PC, workstation, or the like. Using remote networking device 20, a clinician may access data collected by programmer 16, IMD 14, internal sensor 24 and external sensor 22, or information entered by patient 12. Based on analysis of the collected data, the clinician may determine if one or more therapy programs utilized by IMD 14 to deliver the therapy needs to be changed or adjusted. For example, if data collected by IMD system 10 indicates that a program currently utilized by IMD 14 is no longer effective because the therapy is no longer sufficiently strong, the clinician may increase the aggressiveness of the program by, for example, increasing the pulse amplitude signal generated by a neurostimulator. Conversely, if data collected by IMD system 10 indicates that a program currently utilized by IMD 14 is overly aggressive, the clinician may decrease the aggressiveness of the program by, for example, decreasing the pulse amplitude of a signal generated by a neurostimulator.

FIGS. 2A-4 show various embodiments of IMDs that may be used in IMD systems according to the present invention. The examples are not intended to be exhaustive or limiting, and should not be taken as such. Throughout the description of FIGS. 2A-4, reference will be made to components of IMD system 10 shown in FIG. 1. Any of the devices described in reference to FIGS. 2A-4 may be used in an IMD system that includes some or all of the components illustrated in FIG. 1, and may further include any other components described in this specification.

Figure 2A:
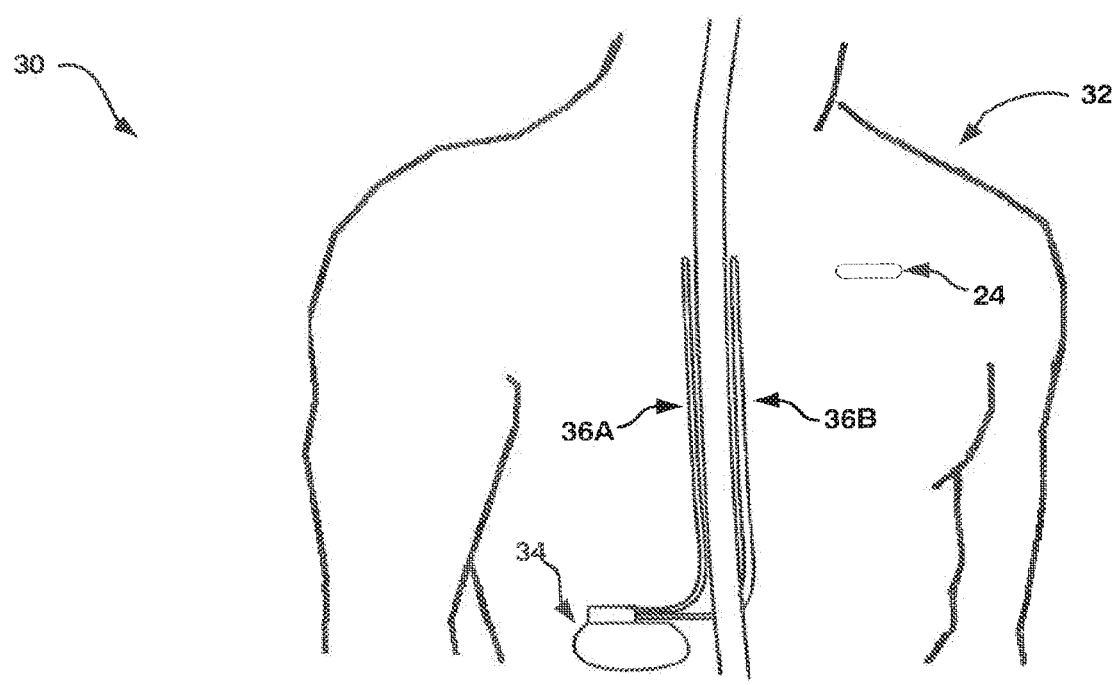
FIG. 2A is a conceptual diagram illustrating an example embodiment of an implantable neurostimulator suitable for use in an IMD system.

FIG. 2A is a diagram illustrating an example IMD system 30 that includes an IMD 34 that takes the form of an implantable spinal cord stimulator, which delivers spinal cord stimulation (SCS) therapy in the form of electrical pulses to a patient 32. However, the invention is not limited to implementation via an IMD 34 that delivers SCS. For example, in some embodiments of the invention, an IMD may take the form of a neurostimulator providing deep brain stimulation, as shown in FIGS. 2B and 2C, which will be discussed below.

In other embodiments of the invention, an IMD may take the form of an implantable pump or implantable cardiac rhythm management device, such as a pacemaker. In still other embodiments of the invention, an IMD may provide, as examples, pelvic floor stimulation, gastrointestinal stimulation, peripheral nerve stimulation, peripheral nerve field stimulation or functional electrical stimulation.

In the illustrated example of FIG. 2A, IMD 34 delivers neurostimulation therapy to patient 32 via electrodes (not shown in FIG. 2A) located on leads 36A and 36B (collectively "leads 36"). Leads 36, as shown in FIG. 2A, be implanted proximate to the spinal cord 18 of patient 32, and SCS 34 may deliver SCS therapy to patient 32 in order to, for example, reduce pain experienced by patient 32. However, the invention is not limited to the configuration of leads 36 shown in FIG. 2A or the delivery of SCS or other pain therapies.

Figure 2B:
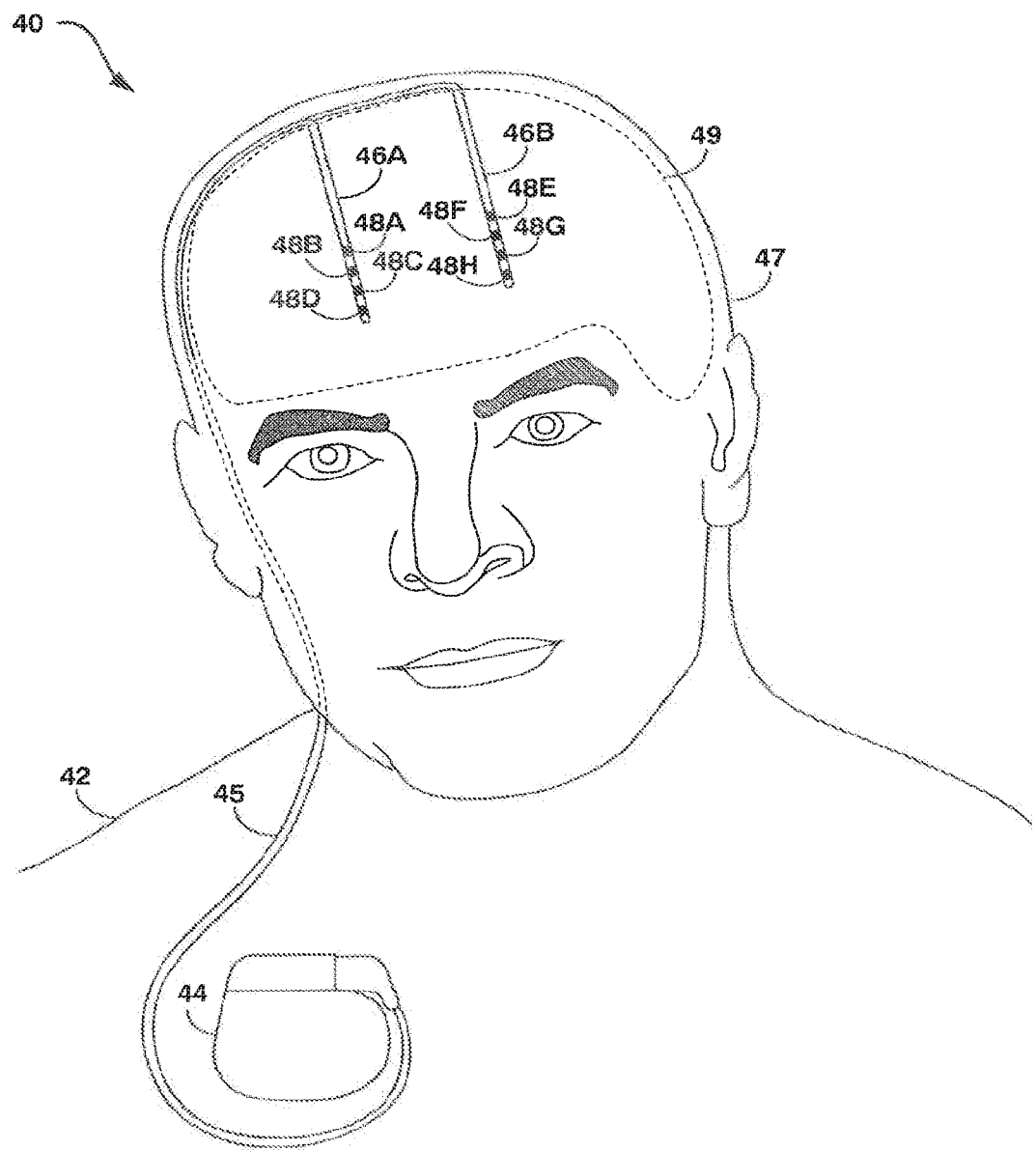
FIG. 2B is a conceptual diagram illustrating another example embodiment of an implantable neurostimulator suitable for use in an IMD system.
Figure 2C:
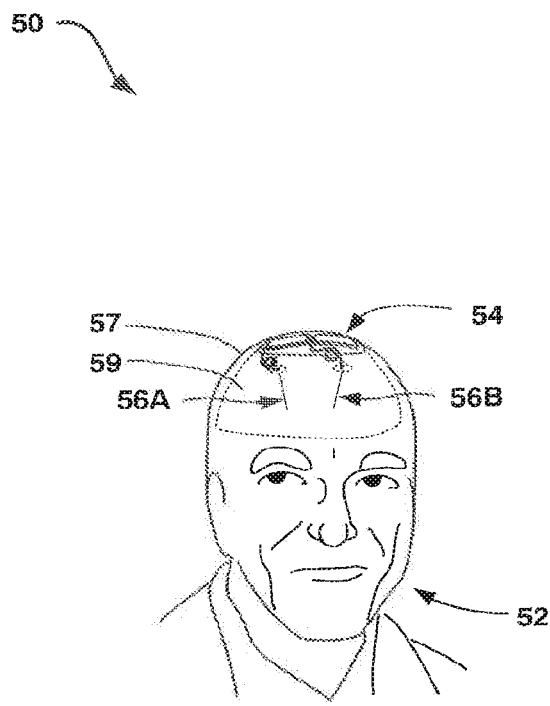
FIG.2C is a conceptual diagram illustrating another example embodiment of an implantable neurostimulator suitable for use in an IMD system.

For example, in another embodiment, illustrated in FIG. 2B, an IMD system 40 includes leads 46A and 46B (collectively "leads 46"), which may extend to the brain 49 of a patient 42, e.g., through the cranium 47 of patient 42. As illustrated in FIG. 2B, leads 46A and 46B respectively include electrodes 48A-D and 48E-H (collectively "electrodes 48"). An IMD 44 may deliver deep brain stimulation (DBS) or cortical stimulation therapy to patient 42 via selected combinations of electrodes 48 to treat any of a variety of neurological disorders, such as movement disorders or psychological disorders, such as tremor, Parkinson's disease, spasticity, epilepsy, depression, mania, bipolar disorder, multiple sclerosis, or obsessive-compulsive disorder. As illustrated in FIG. 2B, leads 46 may be coupled to IMD 44 via one or more lead extensions 45. Leads 46 may be placed within the brain of patient 42 at any of a variety of locations known for DBS applications.

FIG. 2C illustrates another example IMD system 50 in which leads 56 including electrodes (not shown in FIG. 2C) extend from an IMD 54 to the brain 59 of a patient 52 through the cranium 57 of patient 52. In contrast to FIG. 2B, FIG. 2C shows an embodiment in which IMD 54 is implanted proximate to, e.g., on or recessed into, cranium 54.

As further examples, one or more leads may be implanted proximate to the pelvic nerves or stomach, and an IMD may deliver neurostimulation therapy to treat incontinence or gastroparesis. Additionally, leads may be implanted on or within the heart to treat any of a variety of cardiac disorders, such as congestive heart failure or arrhythmia, or may be implanted proximate to any peripheral nerve to treat any of a variety of disorders, such as peripheral neuropathy or other types of chronic pain.

The illustrated numbers and locations of leads and electrodes are merely examples. Embodiments of the invention may include any number of leads, each carrying any number of electrodes, implanted at any of a variety of locations within a patient. Furthermore, the illustrated number and location of IMDs are merely examples. One or more IMDs may be located anywhere within patient according to various embodiments of the invention. More than one IMD may be implanted within a patient to, for example, provide therapy to more than one area of the patient.

The IMDs described herein may deliver therapy according to program, i.e., a set of values for a number of parameters that define the therapy delivered according to that program. In embodiments where an IMD delivers therapy in the form of electrical pulses, the parameters for each therapy parameter set may include voltage or current pulse amplitudes, pulse widths, pulse rates, duration, duty cycle and the like. Further, the IMD may deliver stimulation through a selected subset of an array electrodes, which may be carried by one or more leads, such electrodes 48 of FIG. 2B. A program may include information identifying which electrodes have been selected for delivery of pulses, and the polarities of the selected electrodes. In embodiments in which an IMD delivers other types of therapies, programs may include other therapy parameters, such as drug concentration and drug flow rate in the case of drug delivery therapy. The programs available for use by an IMD may include a number of programs defined by one or more clinicians (not shown), and programs representing adjustments made by a patient to these preprogrammed sets.

IMDs may deliver electrical stimulation to treat and/or reduce the symptoms of any of a variety of disorders. For example, IMDs 44,54 may deliver DBS in order to, for example, reduce the frequency and severity of epileptic seizures experienced by patients 42,52 with epilepsy. As other examples, IMDs 44,54 may deliver DBS in order to reduce the symptoms of a movement disorder or psychological disorder, such as tremor, Parkinson's disease, multiple sclerosis, spasticity, depression, mania, bipolar disorder, or obsessive-compulsive disorder. Additionally, IMD 34 may deliver SCS, or IMDs 44,54 may deliver DBS, to treat chronic pain or sleep apnea.

IMD systems 10, 30, 40 and 50 according to the invention may collect physiological data relating to the efficacy and/or side effects of the administered therapy. In some embodiments, an internal sensor 24 may be used for collection of such data. In further embodiments, an external sensor 22 may be used for collection of such data. This sensor data may be transmitted to an IMD, such as IMD 14, programmer 16 and/or remote networking device 20. In some embodiments, the IMD may include internal sensor 24. In one example, as will be described in greater detail below, IMDs may periodically determine an activity level of a patient based on a signal that varies as a function of patient activity. An activity level may include, for example, a number of activity counts, or a value for a physiological parameter that reflects patient activity.

Additionally, in some embodiments, a patient may enter information relating to activity or efficacy of the therapy into programmer 16 or a separate computing device (not shown) in the form of a journal. The journal may include, for example, any data the patient deems applicable to the administered therapy, such as descriptions of activities, eating, sleep quality, energy level, and the like. This journal may be transmitted to remote computing device 20 and may serve as an additional source of information for a clinician to consider when evaluating the therapy. Sensor data and patient-entered data may be associated in a memory with the one or more programs that were being used by an IMD to deliver therapy at the time such data was generated or entered. The data associated with a particular program may be used to evaluate the program in terms of efficacy and/or side effects.

A clinician may access the one or more programs utilized by an IMD, as well as data collected by the IMD, internal sensor 24, external sensor 22 and/or programmer 16, remotely over network 18 using remote networking device 20. In some embodiments, remote networking device 20 presents a plurality of programs and data to the clinician or other user in the form of a list. Remote networking device 20 may order the list according data, or a user-selected subset of the data, e.g., patient-entered data or sensor data, efficacy data or side effect data, or data regarding a particular one of a plurality of physiological parameters. Furthermore, remote networking device 20 may present sensor or patient-entered data to the clinician in a variety of other forms, such as a trend diagram of data collected by a sensor over time, a patient diary of symptoms (such as pain, seizure or voiding frequency, nutrition or diet), or a histogram or pie chart illustrating percentages of time a parameters, such as patient activity, was within certain ranges.

The clinician may analyze any or all of the collected data to evaluate the efficacy or side effects of one or more programs. For example, delivery of therapy according to one or more programs may result satisfactory therapy efficacy and acceptable side effects. This may be indicated by high patient activity levels when the program is active, for example. The clinician may then create one or more new programs for the IMD that are similar to the current effective program, and potentially more effective, or potentially will induce fewer side effects. Alternatively, the clinician may determine that a program not efficacious, or induces unacceptable side effects. In this case, the clinician may decide to create on or more new programs for the IMD that are less similar to the initial program. Furthermore, the invention is not limited to creation of new programs. In some embodiments, a clinician may analyze the data, and determine modifications to one or more therapy parameters of one or more programs based on the analysis.

In some embodiments, the clinician analyzes the collected data and determines any necessary changes based on intuition or prior experience. In other embodiments, the clinician's analysis may be guided by a specified programming method, for example, a tree diagram based method, or a predetermined progression of programming changes. In some embodiments, the method may be implemented by a computer software program.

When one or more new programs have been created, or one or more program modifications have been determined, the clinician may then upload the programs or modifications from remote network device 20 to programmer 16, or an IMD 14, 34, 44, or 54, via network 18. This therapy titration procedure, including administering therapy, collecting sensor and other patient data, analyzing the collected data and transmitting changes to the therapy based on the analysis of the data may be repeated until an acceptable or "best" program is determined. Advantageously, the entire procedure may be carried out without the patient physically visiting a clinician's office.

Figure 3A:
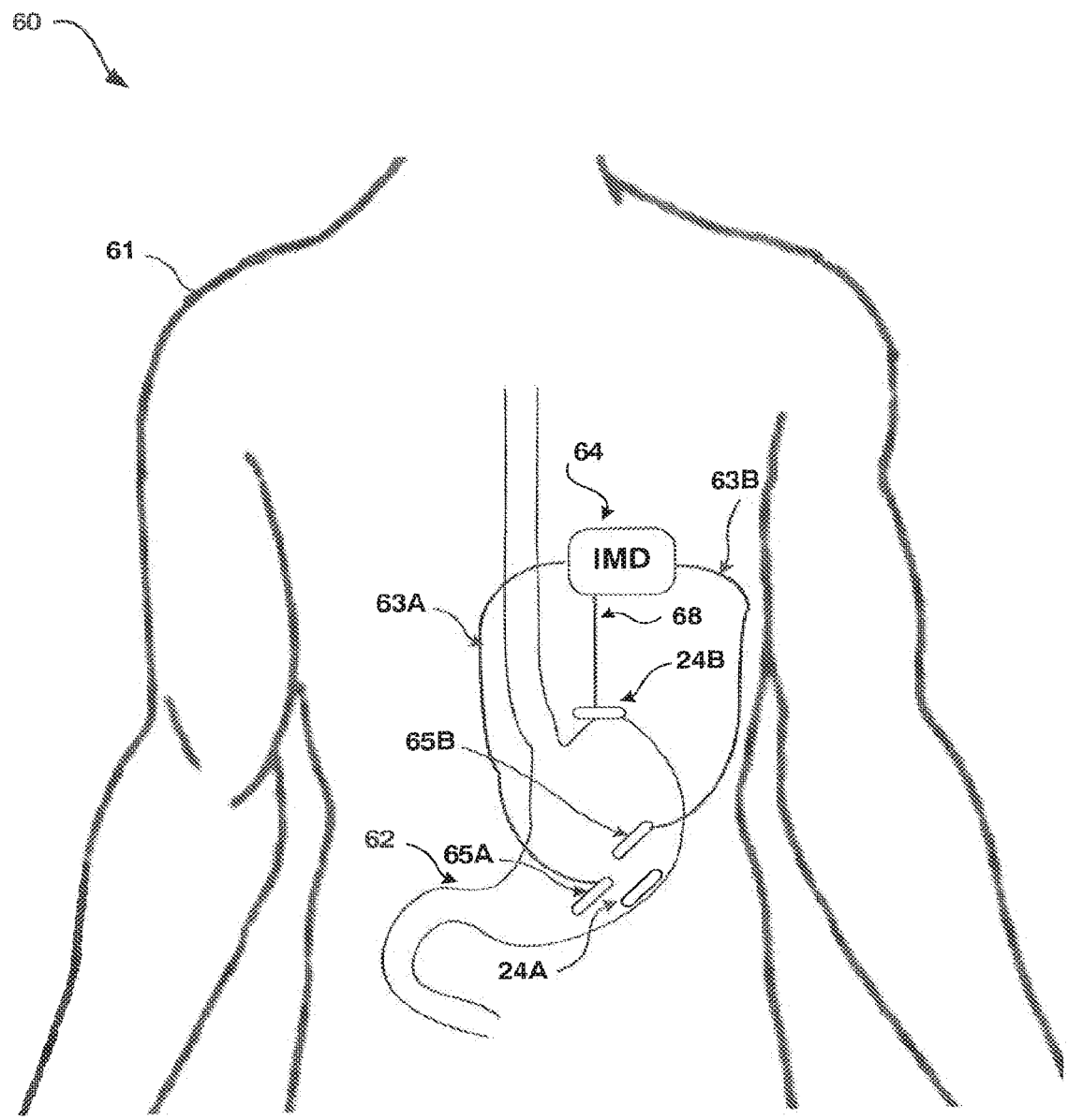
FIG. 3A is a conceptual diagram illustrating an example embodiment of an implantable gastrointestinal stimulator suitable for use in an IMD system.

FIG. 3A is a diagram illustrating another embodiment of an IMD system 60 and IMD 64 according to the invention. FIG. 3A shows a view of a torso of a patient 61, in which stomach 62 is visible. FIG. 3A further illustrates devices for monitoring one or more physiological parameters that indicate the activity of stomach 62, and applying electrical stimulation to the stomach to, for example, induce or reduce symptoms of gastroparesis in response to the monitored parameters.

Physiological parameters such as blood glucose or insulin concentration, core body temperature, distension of the stomach, pH level of the stomach and various plasma enzymes may provide an indication of stomach activity within patient 61. In particular, each of these parameters varies as a function of food intake. As a result, one or more of these physiological parameters can be monitored to detect food intake, and thereby trigger a response, such as delivery of electrical stimulation to stomach 62 of patient 61 to induce or reduce symptoms of gastroparesis, and thereby influence further food intake by the patient.

In the example of FIG. 3A, internal sensors 24A and 24B (hereinafter referred to as "internal sensors 24") sense physiological activity of stomach 62. Sensor 24A is implanted in the body of patient 61, but is external to stomach 62. Sensor 24A is coupled to IMD 64 by a sensor lead 68. Sensor 24B, by contrast, is deployed inside stomach 62, and may communicate with IMD 64 wirelessly. The embodiment is not limited to deployment of two sensors, nor is the embodiment limited to deployment of sensors at the sites shown in FIG. 3A.

Values of the physiological parameters sensed by internal sensors 24 are supplied to IMD 64. For a sensed physiological parameter, IMD 64 may track the parameter over time, measuring the rate of change of the parameter, for example, the amplitude of the parameter, the duration of the parameter, the intensity or concentration of the parameter, or other qualities. In response, IMD 64 may control application of electrical stimulation to the gastric tract, including stomach 62. Simulation electrodes 65A, 65B (hereinafter referred to as "stimulation electrodes 65") are connected to IMD 64 using leads 63A and 63B (hereinafter referred to as "leads 63"). Stimulation electrodes 65 may be affixed to an external surface of the stomach, or other portions of the gastrointestinal tract, via sutures, surgical adhesives, or the like.

IMD 64 may provide electrical stimulation to the stomach 62 through electrodes 65 to induce symptoms of gastroparesis, such as nausea and gastric discomfort, as part of treatment for obesity. The symptoms of gastroparesis discourage caloric intake. In other embodiments, IMD 64 may provide electrical stimulation to stomach 62 through electrodes 65 to reduce symptoms of gastroparesis, for treatment of a patient that suffers from gastroparesis.

IMD 64 may further communicate with one or more external sensors 22, which may sense blood glucose, body temperature, or the like. Furthermore, an external sensor 22 may take the form of a scale, which may provide an indication of the extent to which patient 61 is eating. In some embodiments, sensors 22 and 24 may communicate with programmer 16, which may in turn control delivery of therapy based on the output of the sensors. Additionally, any of sensors 22, 24, IMD 64, or programmer 16 may transmit the sensor date via network 18 to allow a clinician to remotely titrate the therapy administered by IMD 64 using any of the techniques described herein.

Figure 3B:
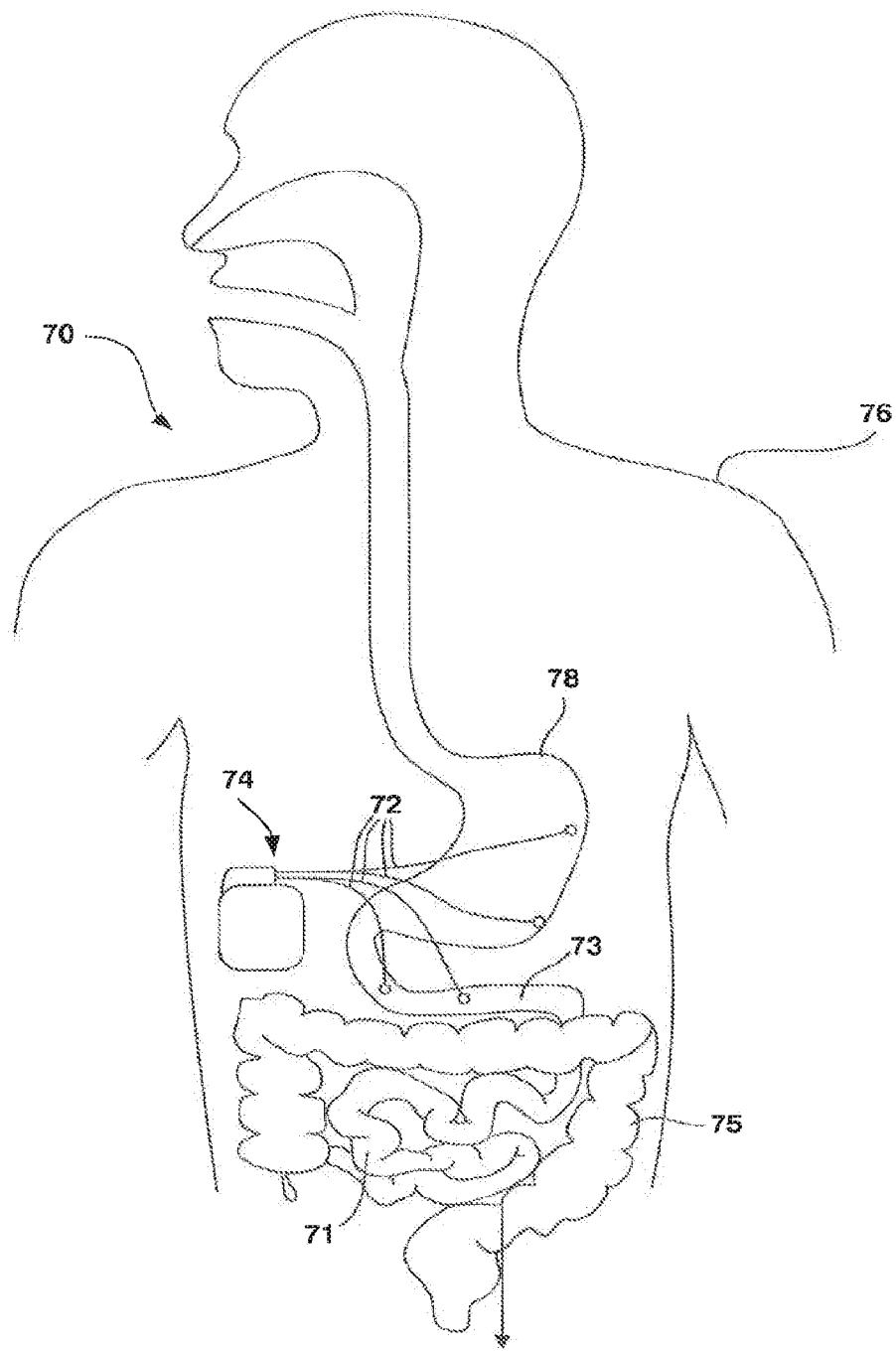
FIG. 3B is a conceptual diagram illustrating another example embodiment of an implantable gastrointestinal stimulator suitable for use in an IMD system.

FIG. 3B is a diagram illustrating another IMD system 70 and IMD 74 according to another embodiment of the invention. IMD 74 delivers electrical stimulation to a patient 76 to regulate caloric intake and thereby alleviate obesity. IMD 74 generates electrical stimulation pulses which are carried away from the IMD to stimulation sites on stomach 78 and small intestine 71 by a plurality of stimulation leads 72. In the example of FIG. 3B, two stimulation leads 72 extend to stomach 78, while two other leads 72 extend to duodenum 73, which forms the proximal segment of small intestine 71. Other portions of small intestine 71, such as the jejunum and ileum, may be similarly stimulated. FIG. 3B also shows large intestine 75, which may also be similarly stimulated. Each stimulation lead 72 carries one or more electrodes (not shown in FIG. 3B) disposed on or within tissue at the outer lining of the stomach 78 and small intestine 71.

IMD 74 may deliver at least two different sets of stimulation pulses to stomach 78 and small intestine 71. A first set of stimulation pulses is delivered to the stomach 78 to induce symptoms of gastroparesis, and thereby suppress appetite and limit food intake. A second set of stimulation pulses is delivered to the small intestine 71 to accelerate food transit and reduce caloric absorption. In this manner, the electrical stimulation limits food intake and caloric absorption, providing a two-pronged therapy for obesity. In a sense, the electrical stimulation delivered by IMD 74 electrically mimics the physiological effects of the Roux-en-Y gastric bypass procedure without the need for surgery.

IMD 74 may generate a first set of stimulation pulses for stomach 78. The first set of stimulation pulses is characterized by a set of therapy parameters, such as amplitude, pulse width and pulse rate, selected to suppress appetite in the patient 76, e.g., by inducing a feeling of fullness or nausea. IMD 74 may also generate a second set of stimulation pulses for small intestine 71. The second set of stimulation pulses is characterized by a set of therapy parameters, such as amplitude, pulse width and pulse rate, selected to increase gastric motility through the small intestine, i.e., accelerate food transit, and thereby reduce caloric absorption in the small intestine. One or both of the first and second stimulation pulses also may be characterized by applicable burst rates and burst durations, for embodiments in which the pulses are delivered in bursts. The burst rates and burst durations may be adjusted by gating a continuous pulse output on and off at appropriate times.

IMD 74 may include one or more internal sensors 24. IMD 74 may also include electronics to communicate with one or more external sensors 22 and programmer 16, as well as electronics for communication with remote network device 20 via network 18. Techniques, such as those described above, may be utilized to allow a clinician to remotely titrate the therapy delivered by IMD 74 based on patient data, such as data gathered via sensors 22, 24, or entered by patient using programmer 16. For example, stimulation intensity associated with stimulation delivered to stomach 78 may be adjusted to increase or decrease feelings of fullness or nausea in the stomach based on sensor data that indicates caloric intake. Similarly, stimulation intensity associated with stimulation delivered to small intestine 71 may be adjusted to increase or decrease motility in the small intestine 71 based on sensor data that indicates caloric intake.

Figure 4:
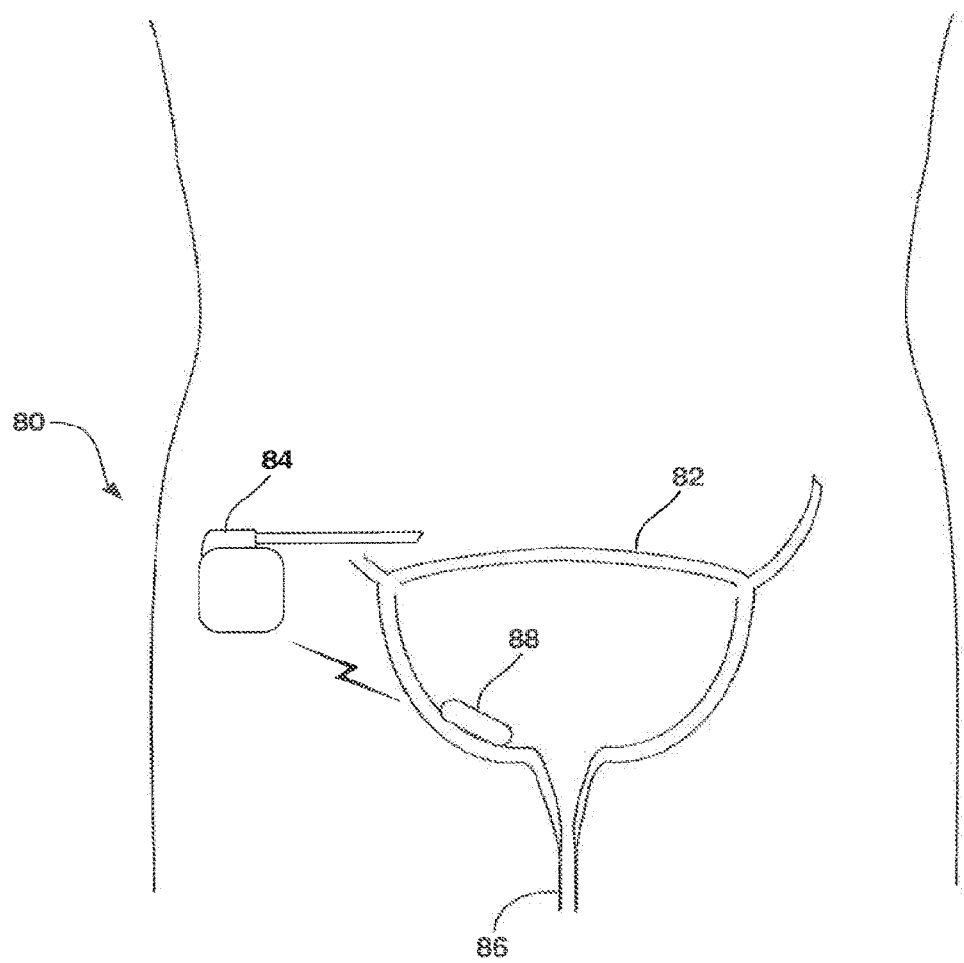
FIG. 4 is a conceptual diagram illustrating an example embodiment of an IMD and urinary tract sensor suitable for use in an IMD system.

FIG. 4 is a schematic diagram illustrating an IMD system 80 including an IMD 84, and urinary tract sensor 88. IMD system 80 is shown in conjunction with a patient and, in particular, a patient bladder 82 and urethra 86 forming part of the patient's urinary tract. Urinary tract sensor 88 is an example of an internal sensor 24. Urinary tract sensor 88 is shown at a target location within bladder 82, but alternatively may be implanted within urethra 86. In some embodiments, multiple urinary tract sensors 88 may be placed within the urinary tract. Urinary tract sensor 88 of FIG. 4 is shown as being implanted within bladder 82. However, urinary tract sensor 88 alternatively may be deployed via a catheter that couples a sensor to an external processing unit.

An implantable urinary tract sensor 88 may be configured to sense one or more physiological conditions within the urinary tract. For example, the physiological conditions may include one or more urodynamic conditions such as urine pressure, urine volume, urine flow, urine pH, temperature, bladder contraction, or urinary sphincter contraction. Hence, in some embodiments, sensor 88 is designed to perform indwelling urodynamic tests. Alternatively, the physiological conditions may include one or more physical characteristics of urine in the urinary tract, such as presence of drug residue, sugar, proteins, blood, keytones, bilirubin, bacteria, yeast cells, and parasites in the urine. Also, sensor 88 may be configured to sense levels of the physical characteristics, such as glucose levels.

Urinary tract sensor 88 may transmit collected sensor data to IMD 84 and/or a programmer 16 (FIG. 1). In the example of FIG. 4, IMD 84 is an implantable neurostimulation device or drug delivery pump. Urinary tract sensor 88 may be capable of continuously or periodically performing urodynamic testing or urinalysis over an extended period of time. IMD 84 and/or programmer 16 may control delivery of therapy based on the sensor data provided by urinary tract sensor 88.

Remote network device 20 may permit a user, such as a clinician, to retrieve physiological information obtained by sensor 88 either directly, or via medical device 84 or programmer 16. Remote network device 20 may process data obtained from sensor 88, and present the information to a user via a display or other output media. The data may include one or more advisories with respect to the presence or level of an urodynamic parameter or urine physical characteristic. The clinician may create a new therapy program or modify an existing program based on the sensor data. The new program or modification may be delivered via network 18 to programmer 16, or to IMD 84 via programmer 16.

IMD 84 responds to such instructions by adjusting the therapy delivered to a patient. In the case of a neurostimulator, for example, IMD 84 may adjust neurostimulation parameters such as amplitude, frequency, pulse width, duration, or electrode configuration. The neurostimulator may include an implantable pulse generator (IPG) coupled to one or more stimulation electrodes, e.g., within the pelvic floor, sacrum, spinal cord, or brain, by one or more leads. In the case of a drug delivery pump, IMD 84 may modify dosage, dosage frequency, dosage time or other parameters. The drug delivery pump may be coupled to one or more catheters that carry one or more drugs from the pump to target locations within, as examples, the pelvic floor, sacrum, spinal cord, or brain.

As examples, a clinician may prescribe new programs or changes to programs responsive to changing physiological conditions such as urine pressure, urine volume, urine flow, urine pH, temperature, bladder contraction, or urinary sphincter contraction. In particular, a clinician may respond to any of the above conditions to assist in voiding, prevent incontinence or otherwise provide therapy to improve urinary tract function.

Figure 5A:
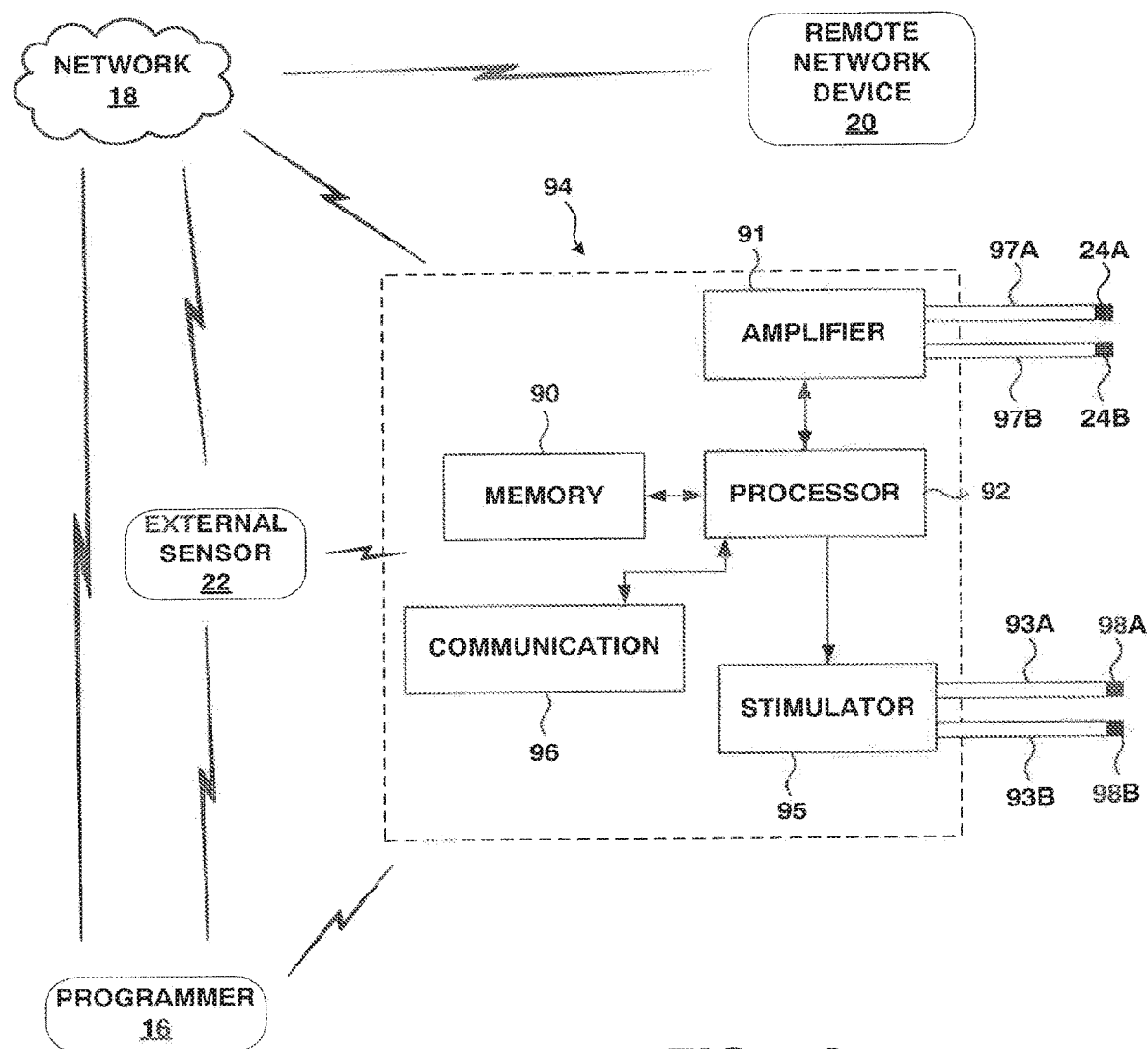
FIG. 5A is a block diagram illustrating an example embodiment of an implantable neurostimulator.

FIG. 5A is a block diagram illustrating an embodiment of an IMD 94 suitable for use in the current invention. IMD 94 may correspond to any of IMDS 14, 34, 44, 54, 64, 74 and 84, discussed above with reference to FIGS. 1-4. IMD 94 may receive instructions, e.g., new programs or modifications to existing programs, from remote networking device 20 via network 18. Network 18 may communicatively couple one or more of IMD 94, programmer 16, and external sensor 22 with remote networking device 20.

IMD 94 comprises a memory 90 that stores existing therapy programs, sensor data, applicable thresholds, or other information pertaining to operation of IMD 104. Memory 90 may also store information about the patient. In addition, processor 92 is programmable, and memory 90 contains program instructions that, when executed by processor 92, cause processor 92 and IMD 94 to provide the functionality ascribed to them herein. Memory 90 may include any form or volatile memory, non-volatile memory, or both. Memory 90 may comprises any one or more of random access memory (RAM), read-only memory (ROM), electronically-erasable programmable ROM (EEPROM), flash memory, or the like.

Stimulator 95 may comprise suitable circuitry for generating an electrical stimulation signal with desired signal characteristics. Stimulator 95 may comprise a pulse generator capable of generating electrical pulses with a desired amplitude, frequency, pulse width and duration. stimulator 95 via leads 93A and 93B (collectively "leads 93") and stimulation electrodes 98A and 98B (collectively "electrodes 98"). Although shown in FIG. 5A as being coupled to two leads 93, each lead 93 comprising one electrode 98, IMD 104, and more particularly stimulator 95, may be coupled to any number of leads 93 comprising any number of electrodes 98. Notably, stimulator 95 need not deliver a stimulation signal continuously, but rather may deliver the stimulation signal in response to an event, or as the result of a received command.

Processor 92 determines whether to deliver an electric stimulation signal to a patient, and controls delivery of the electrical stimulation signal by stimulator 95. More particularly, processor 92 controls stimulator 95 to deliver electrical stimulation with desired characteristics, e.g., pulse amplitude, width and rate, via selected ones of electrodes 98, based on a therapy program stored in memory 90.

In some embodiments, IMD 94 delivers stimulation according to a program group comprising a plurality of programs. Program groups may be stored in memory 90. Processor 92 may control stimulator 95 to deliver stimulation according to a program group by controlling stimulator to alternate delivery of stimulation according to the programs of a group, e.g., switch from program to program of a group on a periodic basis, such as pulse to pulse. For each program of a program group, processor 92 controls delivery of stimulation according to the amplitude, width, rate and electrode combination specified by that program.

Processor 92 may also record the occurrence of electric stimulation within memory 90 for later use. Processor 92 also routes information from the various modules within IMD 94 to an appropriate other module for further use. Processor 92 may comprise any one or more of a microprocessor, application specific integrated circuit (ASIC), digital signal processor (DSP), discrete logic circuitry, or the like.

An amplifier 91 in IMD 94 may receive signals detected by internal sensors 24A and 24B (collectively "internal sensors 24") via sensor leads 97A and 97B (collectively "leads 97"). In some embodiments, one or more of internal sensor 24 are located within a housing of IMD 94. Furthermore, in some embodiments in which one or more of internal sensors 24 are not coupled to IMD 94 via leads 97, amplifier 91 may receive signals from internal sensors 24 via wireless telemetry, i.e. via communication circuitry 96.

In some embodiments, IMD 94 may receive signals from one or more external sensors 22 via communication circuitry 96. Such signals may also be provided to amplifier 91, or may be provided directly to processor 92 for processing. IMD 94 may include or be coupled, e.g., electrically or wirelessly, to any number of sensors 22 and 24. Sensors 22 and 24 may take the form of any type of sensor for sensing any of the physiological parameters described herein.

Amplifier 91 includes circuitry for amplifying, filtering, converting to a digital signal, or otherwise conditioning the received signals for processing by processor 92. In some embodiments, processor 92 may regulate the delivery of therapy by stimulator 95 based on the received signals, i.e., the sensor data. Additionally, in some embodiments, processor 92 may supply the sensor data to communication module 96 to send to remote networking device 20 via network 18 and, in some cases, via programmer 16. In further embodiments, processor 92 may store the sensor data in memory 94 until communication with remote networking device 20 and/or programmer 16 is available.

Communication module 96 may also receive instructions including new programs or program groups, or modifications to existing programs or program groups, from remote network device 20 via network 18 and, in some embodiments, programmer 16. Communication module 96 the supplies the instructions to processor 92. Processor 92 may add to, delete or modify the programs stored in memory 90, and direct stimulator 95 according to the programs stored in memory 90 after the addition, deletion, or modification. Communication module 96 may include circuitry for local communication with programmer 16 and/or external sensors 22, as well as circuitry for accessing network 18, such as RF communication circuitry conforming to one or more of the Bluetooth or 802.11 communication standards, and circuitry conforming to proprietary medical device telemetry standards.

Although the embodiment of FIG. 5A is described as including an IMD 94 that stores the existing programs or program groups for therapy delivery in its memory 90, the invention is not so limited. In other embodiments, the existing programs or groups may be stored in programmer 16, and transmitted to IMD 94 via communication module 96 when selected by a patient. In such embodiments, programmer 16 may receive programs or modifications from remote networking device 20, and accordingly modify the contents of its memory. Furthermore, programmer 16 may collect sensor data from sensors 22 and 24, directly or via IMD 94, and transmit such data to remote networking device 20 via network 18. Also, programmer 16 may collect other patient data, such as diary entries, and transmit such data to remote networking device 20 via network 18.

Figure 5B:
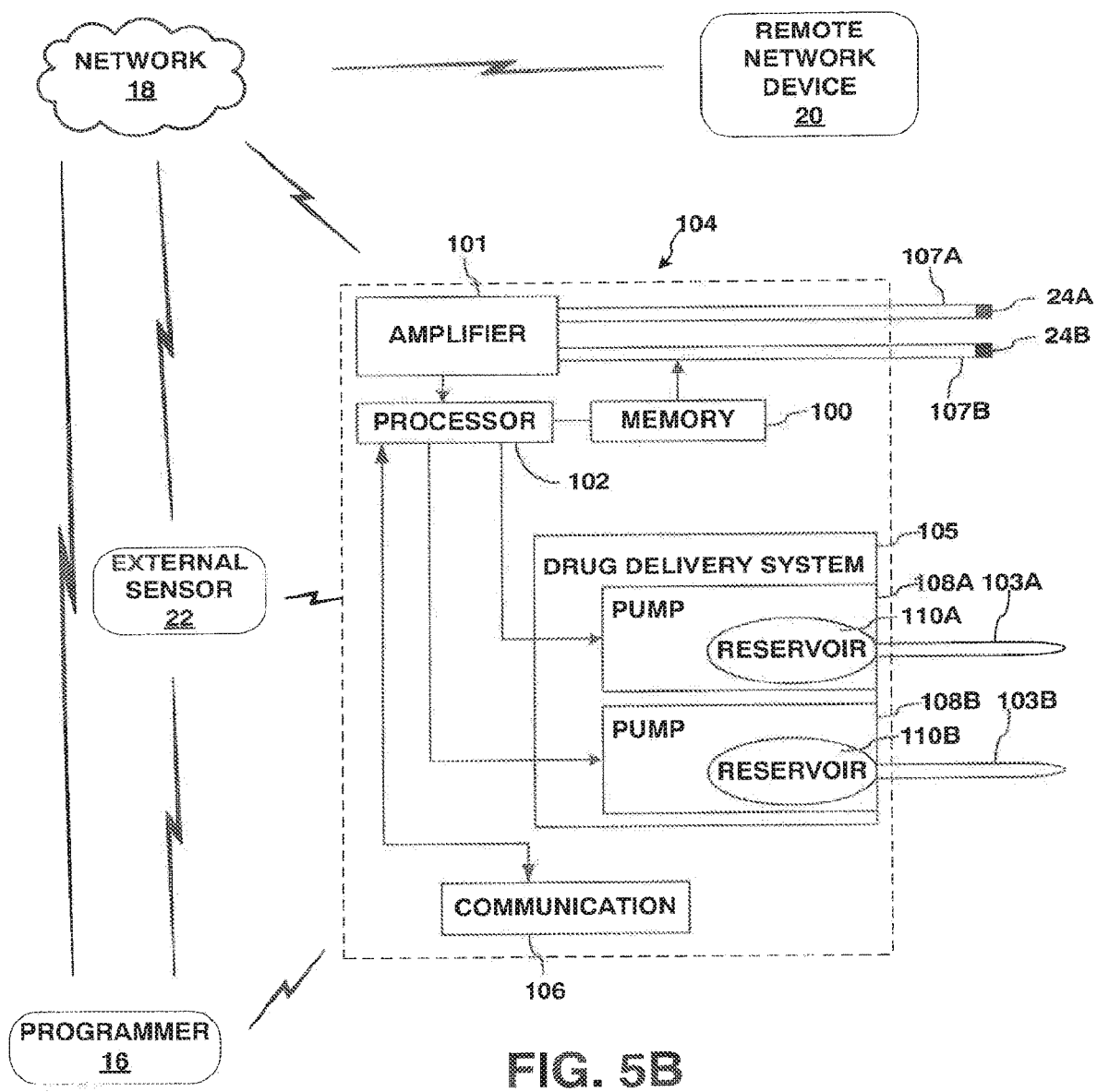
FIG. 5B is a block diagram illustrating an example embodiment of an implantable drug delivery device suitable for use as an IMD in an IMD system.

FIG. 5B is a block diagram illustrating an embodiment of an IMD 104 according to the present invention, which takes the form of an implantable drug delivery device. IMD 104 may be configured to deliver any of a variety of drugs, to any of a variety of locations within a patient, to treat any of a variety of symptoms or disorders.

A non-limiting list of example drugs which may be delivered by IMD 104 includes insulin, glucagon, baclofen, antimuscarinic drugs, anticloinergic drugs, membrane channel drugs, channel blocker drugs, alpha adrenoceptor antagonist drugs, beta adrenoceptor agonist drugs, antidepressant drugs, prostatglandin synthesis inhibitor drugs, motor neuron suppression drugs, sensory desensitization drugs, anti-inflammatory drugs, pain relief drugs, a hormone, tolterodine, trospium, propantheline, atropine, hyoscyamine, darifenacin, solifenacin, calcium antagonists, potassium channel openers, terodiline, oxybuynin, propiverine, flaxoxate, alfuzosin, doxazosin, prazosin, terazosin, tamsulosin, terbutaline, chenbuterol, salbutomol, imipramine, indomethacin, flurbiprofen, resiniferatoxin, capsaicin, dimethyl sulfoxide, bacillus Calmette-Guerin (BCG), estrogen, testosterone, adrenaline, a serotonin uptake inhibitor, a selective serotonin re-uptake inhibitor, ephedrine, norephedrine, propranolol, duloxetine, phenoxybenzamine, bethanechol, carbahol, distigmine, an antibiotic, an analgesic, a tricyclic antidepressant, a muscle relaxant, a smooth muscle relaxant, a hormone replacement agent, a libido enhancer, a vascular dilator, flouroquinolone, trimethoprim-sulfamethoxazole, aspirin, acetaminophen, phenazopyridine, opioids, meperidine, hydromorphone, methandone, levorphanol, morphineglucosamine, chondroitin, quercetin, hyaluronic acid, pentosan polysulfate sodium, heparin sodium, deipramine, nortriptyline, doxepin, oxybutynin chloride, cyclobenzprine, hyoscyamine sulfate, tolterodine tartrate, an anti-diarrheal agent, a motility inhibition agent, a motility stimulation agent, loperamide, alosetron, diphenoxylate, difenoxin, cilansetron, tagaserod, cisapride, erythomycin, caffeine, amitriptyline, sildenafil, L-arginine, phentolamine, amantadine, bupropion, buspione, cypropeptadine, dextroamphetamine, pemoline, yohimbine, vardenafil, tadalafil, prostaglandin, sertraline, paroxetine, levapopa, carbidopa, dopamine agonists, anticholinergics, COMT inhibitors, and clomipramine. IMD 104 may deliver such drugs to, as examples, the spinal cord, brain, intrathecal space, gastrointestinal tract, pelvic floor, sacrum, sex organs, or blood stream of a patient. IMD 104 may deliver such drugs to treat, as examples, pain, movement disorders, psychological disorders, sexual dysfunction, incontinence, constipation, congestive heart failure, or gastroparesis.

IMD 104 includes an amplifier 101 coupled to internal sensors 24 by leads 107A and 107B, a memory 100, a processor 102, and a communication module 106, which are substantially similar to, and provide substantially the same functionality as the corresponding elements of IMD 94 discussed above with reference to FIG. 5B. For example, processor 102 of IMD 104 may provide substantially similar functionality processor 92 of IMD 94 with respect to controlling delivery of therapy based on programs or program groups stored in memory 100, controlling delivery of therapy based on sensor data received from sensors 22,24, transmitting sensor data to remote networking device 20 via network 18, and receiving new programs or program modifications made by a clinician from remote networking device 20 via network 18. However, unlike IMD 94, which provides therapy by delivering electrical stimulation, IMD 104 provides therapy by delivering drugs.

To that end, IMD 104 includes a drug delivery system 105 comprising pumps 108A and 108B (collectively "pumps 108"). Pumps 108 may deliver respective drugs to a patient from respective reservoirs 110A and 110B (collectively "reservoirs 110") via respective infusion apparatus, such as catheters 103A and 103B (collectively "catheters 103"). The invention is not limited to the configuration illustrated in FIG. 5B, and drug delivery system 105 may include any number of pumps 108 and reservoirs 110, coupled to any number of catheters 103. Reservoirs 110 may be self-sealing and may be refilled by a needle and syringe, such that drug delivery system 105 need not be surgically removed when reservoirs 110 are empty. Pumps 108 may further include a fill port (not shown) for refilling the reservoirs 110.

Processor 102 may control the delivery of the drug by each of pumps according to a respective program. The program for each of pumps may comprise respective values for therapy parameters such as flow rate, concentration, bolus duration or timing, or the like. Collectively, the programs for each of pumps 108 may be considered a program group.

Figure 6:
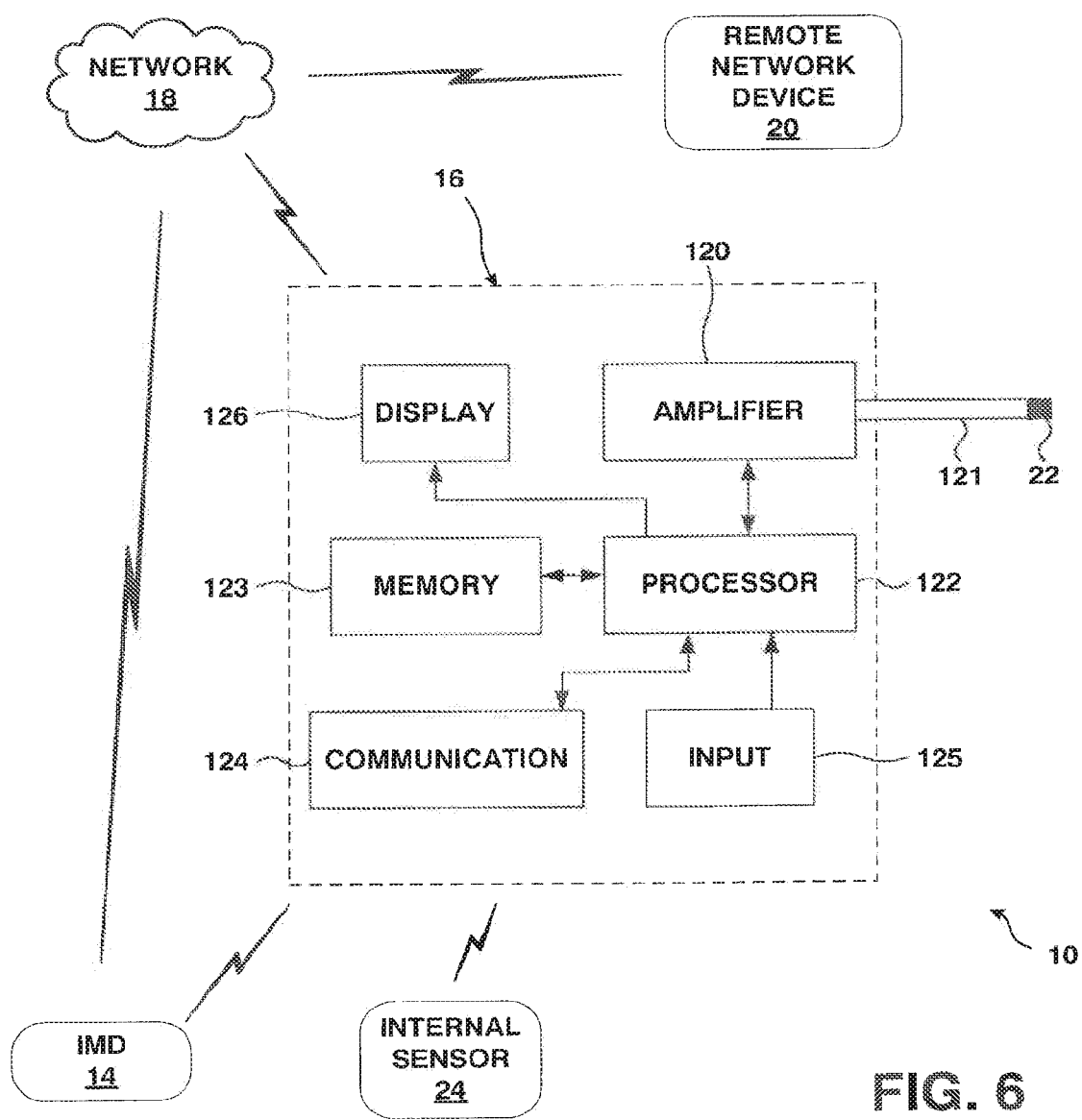
FIG. 6 is a block diagram illustrating an example embodiment of a programmer suitable for use in an IMD system.

FIG. 6 is a block diagram illustrating programmer 16 in greater detail. Programmer 16 may include or be coupled to one or more external sensors 22, which collect data relating to an efficacy or side effect of a therapy being administered to a patient by IMD 14. In the example of FIG. 6, external sensor 22 is coupled to programmer 16 by a lead 121. In other embodiments, external sensor 22 is wirelessly coupled to programmer 16 via a communication module 124, or included within a housing of programmer 16. Although illustrated with reference to IMD system 10 and IMD 14, programmer 16 may be a component of any of the IMD systems described herein.

External sensor 22 may be used to measure a wide variety of physiological parameters, for example, blood glucose or insulin concentrations, patient body temperature, patient activity, and the like. Sensors that may be used include accelerometers, electrodes, electrochemical sensors, and the like. In some embodiments, programmer 16 may be worn or carried by a patient, which may allow, for example, a programmer 16 including an accelerometer to measure activity levels continuously. In other embodiments programmer 16 is a device which a patient may intermittently interact with. During these interactions, external sensor 22 may collect data from the patient.

External sensor 22 transmits a signal to an amplifier 120. Amplifier 120 may include circuitry to filter, amplify, convert to a digital signal, or otherwise process the signal before supplying the signal to processor 122. Processor 122 processes signal and may supply the resulting sensor data to a memory 123, which may store the data. Additionally, processor 122 may supply the sensor data or a portion of the sensor data to a display 126, for display to a user such as a patient or clinician. In some embodiments, display 126 may allow a patient to monitor his or her own therapy on an intermittent or a continuous basis.

Display 126 may be any suitable display technology, for example, LED lights, a LCD panel, a CRT display, or the like. Memory 123 may include any form of removable, fixed, volatile memory, non-volatile memory, or both. Memory 123 may comprises any one or more of RAM, ROM, EEPROM, flash memory, or the like. Processor 92 may comprise any one or more of a microprocessor, ASIC, DSP, discrete logic circuitry, or the like.

Programmer 16 may further include an input device 125. Examples of suitable input devices include touch screen, buttons, a keyboard, pointing device, microphone, or the like. Input device 125 may allow a patient to input additional information that pertains to the efficacy and/or side effects of the patient's therapy. For example, a patient may input descriptions of activities, eating, sleep quality, energy level, a log of seizure frequency or severity, voiding logs for incontinence disorders, diet or nutrition journals, ratings of efficacy or side effects, particular side effects, or the like. This journal or diary, as well as sensor data collected by programmer 16, may be transmitted to remote computing device 20 via network 18 as patient data for a clinician to consider when evaluating the therapy.

Processor 122 may supply the data or a portion of the data to a communication module 124 for transmission via network 18. In some embodiments, communication module 124 may communicate with IMD 14 and/or internal sensors 24, as well as network 18. In some embodiments, programmer 16 may transmit data collected by internal sensor 24 to remote networking device 20 via network 18. Programmer 16 may receive data, which has been collected by an internal sensor 24, directly from the sensor or from IMD 14. Programmer 16 may then forward the data to network 18 for retrieval by remote network device 20. In other embodiments, as discussed above, IMD 14 and/or sensors 24 may communicate directly with network 18.

In some embodiments, a clinician may access the patient data via remote network device 20. The clinician may utilize the data to evaluate an efficacy or extent of side effects of the current therapy. For example, IMD 14 may be a neurostimulator providing pain relief therapy. Data collected by sensors 22,24 to evaluate the efficacy of the pain relief therapy may include activity levels. For example, if a patient's activity level as measured by an accelerometer (e.g. implanted or included in a wearable programmer 16) is decreasing, it may be determined that the patient is experiencing increasing amounts of pain. In response, a clinician may define a program, or modify an existing program, for the pain relief therapy. The resulting program may include an increased pulse amplitude, a different pulse length, a higher pulse rate, or the like.

The clinician may then transmit program or program modification from remote network device 20 to communication module 124 of programmer 16 via network 18. Communication module 124 may transmit the new set of therapy parameters from programmer 16 to IMD 14.

Figure 7:
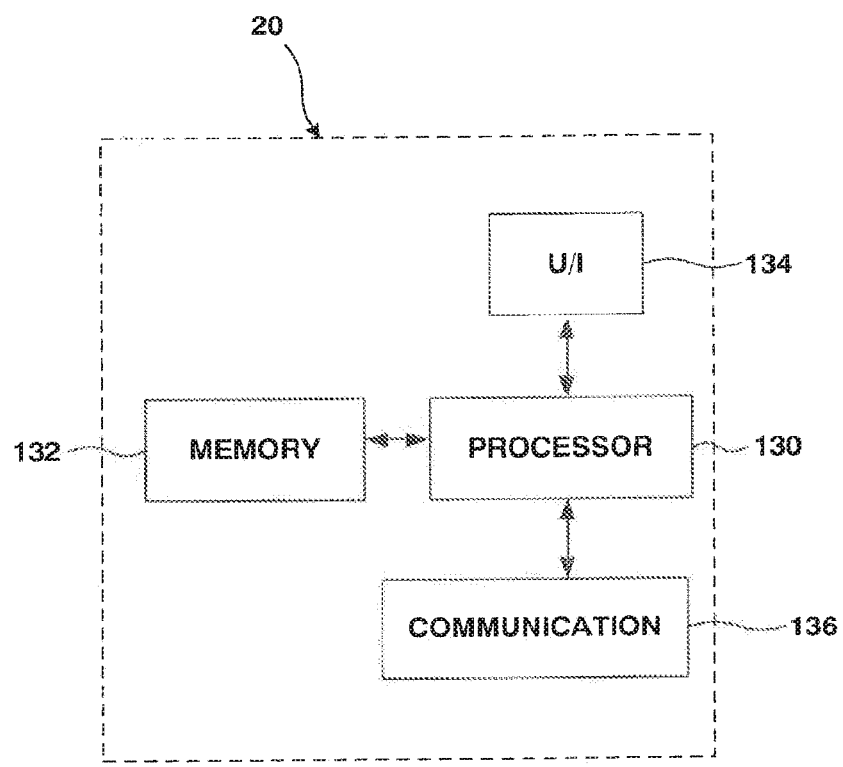
FIG. 7 is a block diagram illustrating an example embodiment of a remote networking device.

FIG. 7 is a block diagram illustrating an example embodiment of a remote networking device. As illustrated in FIG. 7, remote networking device may comprises a processor 130, a memory 132, a user interface (U/I) 134, and a communication module 136. Processor 130 may comprise any one or more of a microprocessor, ASIC, DSP, or discrete logic circuitry. Memory 132 may comprise any fixed or removeable media, such as RAM, ROM, a CD-ROM, a hard disk, EEPROM, flash memory, or the like. Memory 132 may store program instructions that, when executed by processor 130, cause processor 130 and remote networking device 20 to provide the functionality ascribed to them herein.

Using communication module 136, processor 130 may receive patient data, including sensor data, from an IMD system via network 18. Communication module 136 may include any circuitry known to be suitable for accessing a computer network. Processor 130 may present the patient data to a user, such as a clinician, via U/I 134, which may include a display and at least one input device, such as keyboard, keypad, or pointing device. The user may determine a programming change based on patient data, and enter the programming change via U/I 134. Using the communication module, processor 130 may transmit the programming change to the IMD system via the network. In some embodiments, processor 130 may automatically or semiautomatically, e.g., provided as a suggestion for user approval, determine programming changes. Such automatic or semi-automatic determinations may be based on traversal of a programming tree structure or predetermined progression of program changes, described below with reference to FIGS. 10 and 11, which may be stored in memory 132.

Figure 8A:
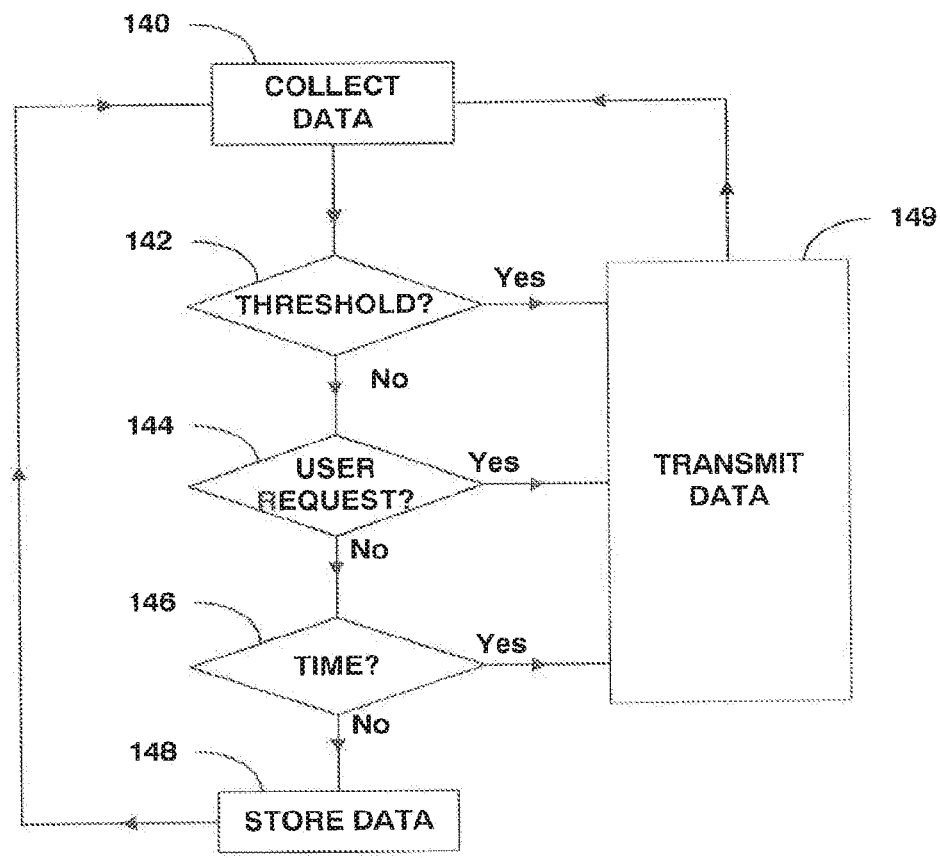
FIG. 8A is a flow diagram illustrating an example process by which a processor controls collection and transmission of patient data by one or more devices in an IMD system.

FIG. 8A is a flow diagram illustrating a process performed by IMD 14. The process of FIG. 8A may be performed by any of the IMDs, or other devices within a programming system described herein. IMD 14 may continuously or intermittently measure a patient's physiological data relating to an administered therapy (140). Physiological data, i.e., sensor data, may be measured using any of the sensors described above, for example. Upon measurement of the data, IMD 14 proceeds to determine if a value of the data is above a threshold (142). For example, IMD 14 may determine if a set number of therapy events have occurred, or may determine if a physiological parameter is above or below a threshold, such as a blood sugar level. If the threshold has been met (142), IMD 14 will transmit any collected data to programmer 16 and/or remote network device 20 via network 18 (149).

If the threshold has not been met (142), IMD 14 proceeds to determine if a user has requested transfer of any data stored in the memory of IMD 14 (144). A user may include, for example, a patient, clinician, or other authorized user. A patient may request transmission of data in response to an event, such as an occurrence of undesired side effects or symptoms. Additionally, a patient may request transmission of data in preparation for an appointment with a clinician, or because therapy is no longer producing acceptable results. A clinician may request transfer of the data for any of the same reasons, and may also request data transfer as part of a therapy titration method, to monitor therapy, or the like. If the user has requested transfer (144), IMD 14 will transmit any collected data to programmer 16 and/or remote network device 20 via network 18 (149).

If the user has not requested transfer (144), IMD 14 will determine whether a specified time 146 has occurred (146). The time may be specified as an interval of time since the last transmission. In some embodiments, the time is a scheduled instant or period, such as once an hour, once a day, every other day, and the like. If the specified time has been met (146), IMD 14 transmits any collected data to programmer 16 and/or remote network device 20 via network 18 (149). If the specified time 146 has not been met, the data may be transferred to a memory for storage until a patient data transmission is desired or specified (148).

Figure 8B:
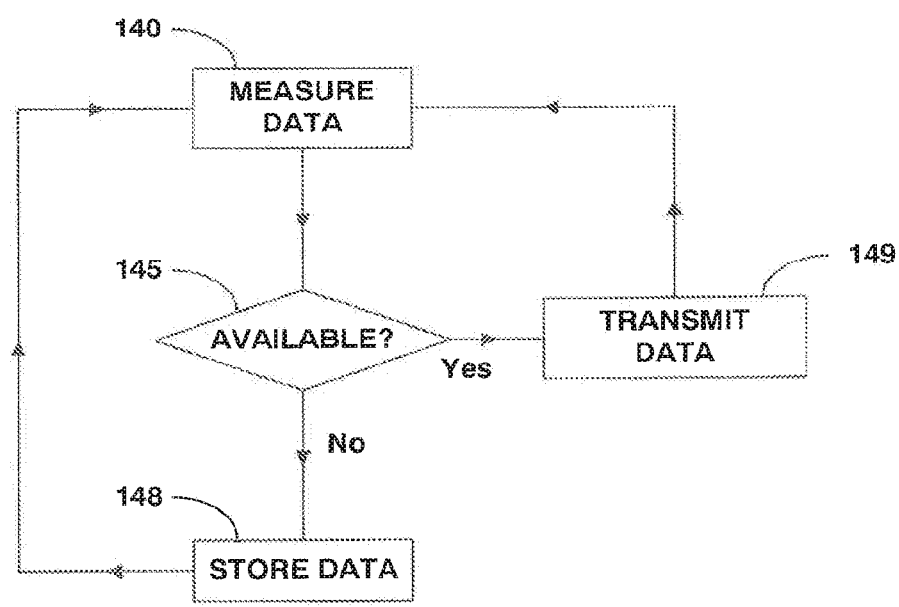
FIG. 8B is a flow diagram illustrating another example process by collection and transmission of patient data by one or more devices in an IMD system.

FIG. 8B is a flow diagram illustrating another process which may be performed by IMD 14, any of the IMDs, or other devices within a programming system described herein. The process is similar to that which was described in reference to FIG. 8A; however, upon measurement of physiological parameters relating to an efficacy or side effect of a therapy (140), IMD 14 determines if network 18 or programmer 16 are available to receive transmitted data (145). In some embodiments, programmer may not be carried or worn by patient continuously, so direct data transmission from IMD 14 to programmer 16 may not always be available. In some embodiments IMD 14 may connect directly to network 18. In these embodiments, IMD 14 may not always be able to connect to network 18. For example, a patient utilizing IMD 14 may have traveled out of the range of network 18, or network 18 may be busy.

If programmer 16 and/or network 18 is available (145), IMD 14 transmits data (149). If programmer 16 and/or network 18 is unavailable, IMD 14 stores the collected data in memory (148). IMD 14 may determine the availability of programmer 16 and/or network 18 after each data measurement, as shown in FIG. 8B. Alternatively, in some embodiments, IMD 14 may determine the availability of programmer 16 and/or network 18 at predetermined intervals after an initial unavailable determination.

Figure 9:
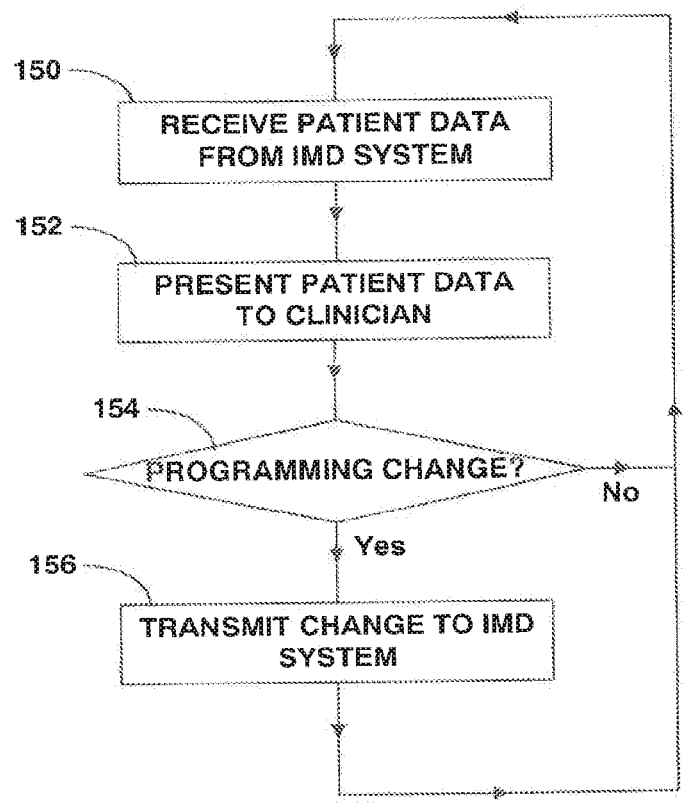
FIG. 9 is a flow diagram illustrating an example operation of a remote networking device during remote therapy titration.

FIG. 9 is a flow diagram illustrating an example process which may be performed by a remote networking device 20 according to the present invention. As illustrated in FIG. 9, remote networking device 20 may receive patient data from an IMD system (150). The patient data may include sensor data, as well as diary or journal information, or other information entered by the patient using programmer 16. The patient data may be transmitted by any device of an IMD system, such as one or more of internal or external sensors, the IMD, or a programmer.

Remote networking device 20 may then present the patient data to a user, such as a clinician (152). The patient data may reflect the efficacy of, or side effects resulting from, delivery of therapy according to one or more current programs. Based on the patient data, the user may determine that a programming change is necessary or desirable (154). The programming change may comprise one or more new therapy programs, or changes to one or more parameters of one or more existing programs. The remote networking device 20 may transmit such changes to the programming system via network 18, e.g., to the IMD or programmer (156).

Figure 10:
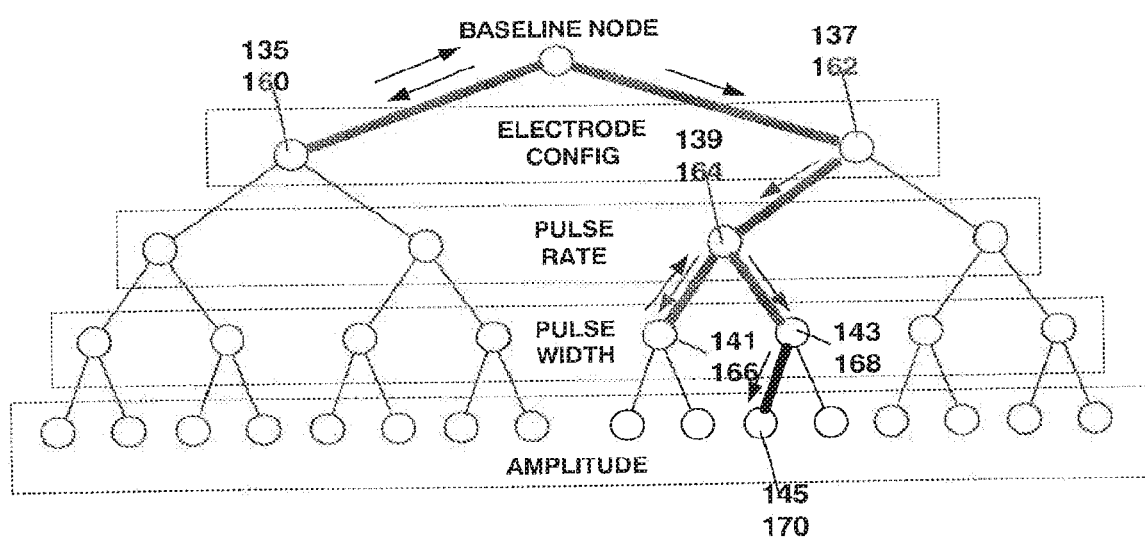
FIG. 10 is a tree diagram illustrating another example process by which therapy is remotely titrated.

Remote titration of a therapy program administered by an IMD may be further implemented using directed programming. In some embodiments, a clinician may utilize a computer software program on remote network device 20 to enable more efficient programming of the IMD. For example, FIG. 10 is a diagram illustrating traversal of a therapeutic tree to define an example program path. As shown in FIG. 10, the program path first traverses from the baseline node downward to a first node 160 in level 1, which defines a particular electrode combination and/or polarity.

The clinician may transmit a program comprising the electrode combination to the IMD or programmer via network 18. The IMD then implements that program by delivering therapy according to the program. The IMD, internal sensor, external sensor, and/or programmer collect data relating to an efficacy or side effect of the program. Such data is transmitted to remote networking device 20 via network 18. The clinician may then determine another program to try based on analysis of the patient data. This procedure may be repeated at each node on the therapeutic tree.

In this example, the efficacy improvement or side effect reduction produced by node 160 relative to the patient's baseline condition, i.e., without therapy, is less than a specified threshold level, e.g., 50%. Accordingly, the program path progresses no further down the path connected to node 160, and instead reverses through the baseline node to the second node 162 at level 1. In this case, node 162 presents an efficacy or side effect improvement in excess of 50%, and the program path proceeds to the next node 164, which resides in level 2 and specifies a change in pulse rate, while maintaining the electrode configuration and other parameters of node 162.

Node 164 defines stimulation parameters that are found to yield an efficacy or side effect improvement in excess of 50%. As a result, the program path continues along a path connected to node 164. In particular, the program path first evaluates parameters associated with node 166 in level 3. Node 166 represents an adjustment to pulse width, while maintaining the electrode configuration and pulse rate specified by node 164. However, the efficacy feedback reveals that node 166 does not achieve an efficacy or side effect improvement of greater than 50%. For this reason, the program path returns to node 164 and traverses another branch of node 164 to node 168.

At node 168, the stimulation parameters produce an efficacy or side effect improvement in excess of 50% relative to the baseline condition of the patient. In response, the program path proceeds to node 170 in level 4, which represents a change in amplitude but otherwise maintains the parameter values associated with node 168 in level 3.

Generally, a 50 percent efficacy or side effect improvement relative the baseline patient condition is required to continue along a path extending from a particular node. However, once a program path reaches the bottom of the tree, e.g., level 4, additional program paths may still be created until a higher improvement is reached, e.g., 80%.

Once patient 12 is experiencing an 80 percent improvement relative to the baseline condition along a given program path, the process may be terminated at the current node in that program path or the process may only proceed to fine tune parameters using lower levels along the same path. As mentioned previously, the 50% and 80% thresholds are only examples, and the clinician may set them to any percentage of improvement, where 100 percent improvement may mean there are no symptoms or side effects during therapy.

Other alternative embodiments are also within the scope of the invention. For example, for therapies that have a well defined treatment ladders, such as therapies that vary in a known way over some time period, remote networking device 20 may transmit a sequence, list, or table of predetermined therapy programs or adjustments to the IMD. For example, the formation of scar tissue after implantation of the IMD may necessitate a gradual increase in stimulation intensity to overcome the increased impedance due to the scar tissue. As a second example, a patient may require increased drug dosages to overcome increasing physiological tolerances. The therapy programs or adjustments of a predetermined sequence, list, or table may be transmitted one step at a time, such as the remote networking device 20 transmitting an entirely new program. In other embodiments, a sequence of therapy programs or parameter adjustments may be preloaded on the IMD, and remote networking device 20 may transmit a command that causes the IMD to execute a subsequent therapy program or adjustment in the sequence. In some embodiments, the latter approach may be preferred for the patient's security and safety, because less information is transmitted.

Figure 11:
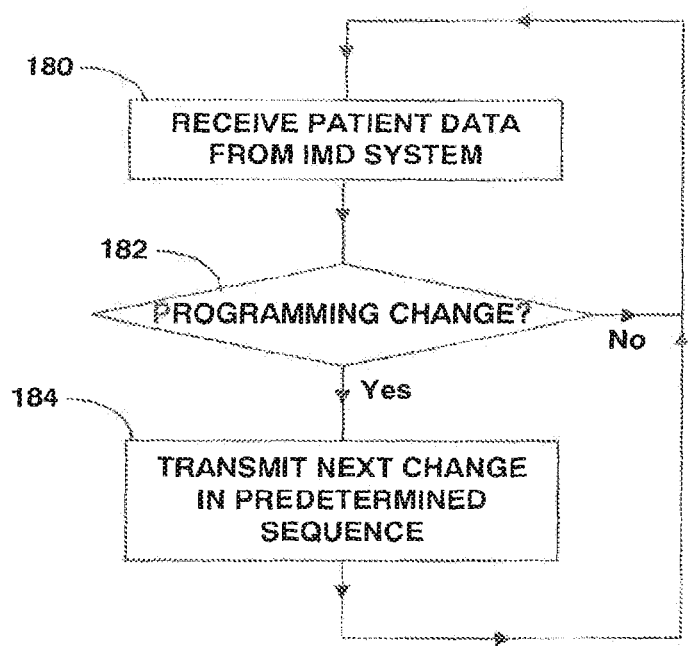
FIG. 11 is a flow diagram illustrating another example process by which therapy is remotely titrated.

FIG. 11 is a flow diagram illustrating another example process by which therapy is remotely titrated according to predetermined therapy programs or adjustments, e.g., a sequence, list, or table of therapy adjustments. According to the example process of FIG. 11, a remote networking device receives patient data from an IMD system (180). Based on an analysis of the patient data, the remote networking device and/or a user determines whether a programming change is indicated (182). If a programming change is indicated, the remote networking device transmits the next programming change in a predetermined sequence, list, table, or the like, e.g., transmits the actual programming change, or a "next" command (184).

Various embodiments of the invention have been described. These and other embodiments are within the scope of the following claims.

What is claimed is:

1. A method comprising:
    delivering, by an implantable medical device (IMD) system, a therapy to a patient according to a first therapy program;
    generating, by the IMD system, patient data that relates to at least one of an efficacy or a side effect of the therapy;
    transmitting, by the IMD system and via a network, the patient data to a remote networking device;
    receiving, by the remote networking device, the patient data;
    analyzing, by the remote networking device, the patient data over a period of time with respect to a baseline condition of the patient to identify a change in the at least one of the efficacy or the side effect of the therapy over the period of time;
    determining, by the remote networking device and based on the change in the at least one of the efficacy or the side effect of the therapy over the period of time, a programming change to the first therapy program, wherein the programming change comprises changing from the first therapy program to a second therapy program defining at least one therapy parameter that is different from at least one therapy parameter of the first therapy program;
    outputting, by the remote networking device and to a user, the programming change to the first therapy program;
    receiving, by the remote networking device and from the user, an input indicating approval of the programming change to the first therapy program;
    transmitting, from the remote networking device to the IMD system via the network, at least one of the programming change or a command to implement the programming change; and
    delivering, by the IMD system, the therapy to the patient according to the second therapy program.

2. The method of claim 1,
    wherein generating the patient data that relates to the at least one of the efficacy or the side effect of the therapy comprises sensing, by a physiological sensor of the IMD system, values of a physiological parameter of the patient over the period of time, and
    wherein analyzing the patient data over the period of time comprises analyzing the values of the physiological parameter of the patient over the period of time with respect to the baseline condition of the patient to identify the change in the at least one of the efficacy or the side effect of the therapy over the period of time.

3. The method of claim 1,
    wherein generating the patient data that relates to the at least one of the efficacy or the side effect of the therapy comprises receiving, by an external programmer of the IMD system and from the patient, at least a portion of a patient diary that relates to the at least one of the efficacy or the side effect of the therapy,
    wherein analyzing the patient data over the period of time comprises analyzing the at least a portion of a patient diary that relates to the at least one of the efficacy or the side effect of the therapy with respect to the baseline condition of the patient to identify the change in the at least one of the efficacy or the side effect of the therapy over the period of time.

4. The method of claim 1,
    wherein generating the patient data that relates to the at least one of the efficacy or the side effect of the therapy comprises sensing, by an IMD of the IMD system, an activity level of the patient over the period of time, and
    wherein analyzing the patient data over the period of time comprises analyzing the activity level of the patient over the period of time with respect to the baseline condition of the patient to identify the change in the at least one of the efficacy or the side effect of the therapy over the period of time.

5. The method of claim 1,
    wherein generating the patient data that relates to the at least one of the efficacy or the side effect of the therapy comprises sensing, by an IMD of the IMD system, a posture of the patient over the period of time, and
    wherein analyzing the patient data over the period of time comprises analyzing the sensed posture of the patient over the period of time with respect to the baseline condition of the patient to identify the change in the at least one of the efficacy or the side effect of the therapy over the period of time.

6. The method of claim 1,
wherein delivering the therapy to the patient comprises delivering spinal cord stimulation (SCS) therapy to reduce pain experienced by the patient,
wherein generating the patient data that relates to the at least one of the efficacy or the side effect of the therapy comprises generating data that relates to at least one of patient motion or patient posture over the period of time, and
wherein analyzing the patient data over the period of time comprises analyzing the data that relates to the at least one of patient motion or patient posture over the period of time with respect to the baseline condition of the patient to identify the change in the at least one of the efficacy or the side effect of the therapy over the period of time.

7. The method of claim 1,
wherein delivering the therapy to the patient comprises delivering therapy configured to treat urinary incontinence of the patient, and
wherein generating the patient data that relates to the at least one of the efficacy or the side effect of the therapy comprises generating data that relates to at least one of urine pressure, urine volume, urine flow, urine pH, temperature, bladder contraction, or urinary sphincter contraction of the patient over the period of time, and
wherein analyzing the patient data over the period of time comprises analyzing the data that relates to the at least one of urine pressure, urine volume, urine flow, urine pH, temperature, bladder contraction, or urinary sphincter contraction of the patient over the period of time with respect to the baseline condition of the patient to identify the change in the at least one of the efficacy or the side effect of the therapy over the period of time.

8. The method of claim 1,
wherein delivering the therapy to the patient comprises delivering therapy configured to treat a gastrointestinal disorder of the patient, and
wherein generating the patient data that relates to the at least one of the efficacy or the side effect of the therapy comprises generating data that relates to at least one of blood glucose concentration, insulin concentration, core body temperature, distension of a stomach, or pH level of a stomach of the patient over the period of time, and
wherein analyzing the patient data over the period of time comprises analyzing the data that relates to the at least one of blood glucose concentration, insulin concentration, core body temperature, distension of a stomach, or pH level of a stomach of the patient over the period of time with respect to the baseline condition of the patient to identify the change in the at least one of the efficacy or the side effect of the therapy over the period of time.

9. A system comprising:
an implantable medical device (IMD) system comprising:
  an IMD configured to deliver a therapy to a patient according to a first therapy program; and
  at least one device configured to:
    generate patient data that relates to at least one of an efficacy or a side effect of the therapy; and
    transmit, via a network, the patient data to a remote networking device; and
the remote networking device, configured to:
  receive the patient data;
  analyze the patient data over a period of time with respect to a baseline condition of the patient to identify a change in the at least one of the efficacy or the side effect of the therapy over the period of time;
  determine, based on the change in the at least one of the efficacy or the side effect of the therapy over the period of time, a programming change to the first therapy program, wherein the programming change comprises changing from the first therapy program to a second therapy program defining at least one therapy parameter that is different from at least one therapy parameter of the first therapy program;
  output, to a user, the programming change to the first therapy program;
  receive, from the user, an input indicating approval of the programming change to the first therapy program; and
  transmit, to the IMD system via the network, at least one of the programming change or a command to implement the programming change,
wherein the IMD system is further configured to deliver the therapy to the patient according to the second therapy program.

10. The system of claim 9,
wherein to generate the patient data that relates to the at least one of the efficacy or the side effect of the therapy, the IMD system comprises a physiological sensor configured to sense values of a physiological parameter of the patient over the period of time, and
wherein to analyze the patient data over the period of time, the remote networking device is configured to analyze the values of the physiological parameter of the patient over the period of time with respect to the baseline condition of the patient to identify the change in the at least one of the efficacy or the side effect of the therapy over the period of time.

11. The system of claim 9,
wherein to generate the patient data that relates to the at least one of the efficacy or the side effect of the therapy, the IMD system comprises an external programmer configured to receive, from the patient, at least a portion of a patient diary that relates to the at least one of the efficacy or the side effect of the therapy, and
wherein to analyze the patient data over the period of time, the remote networking device is configured to analyze the at least a portion of a patient diary that relates to the at least one of the efficacy or the side effect of the therapy with respect to the baseline condition of the patient to identify the change in the at least one of the efficacy or the side effect of the therapy over the period of time.

12. The system of claim 9,
wherein to generate the patient data that relates to the at least one of the efficacy or the side effect of the therapy, the IMD is configured to sense an activity level of the patient over the period of time, and
wherein to analyze the patient data over the period of time, the remote networking device is configured to analyze the activity level of the patient over the period of time with respect to the baseline condition of the patient to identify the change in the at least one of the efficacy or the side effect of the therapy over the period of time.

13. The system of claim 9,
wherein to generate the patient data that relates to the at least one of the efficacy or the side effect of the therapy, the IMD is configured to sense a posture of the patient over the period of time, and
wherein to analyze the patient data over the period of time, the remote networking device is configured to analyze the sensed posture of the patient over the period of time with respect to the baseline condition of the patient to identify the change in the at least one of the efficacy or the side effect of the therapy over the period of time.

14. The system of claim 9,
wherein to deliver the therapy to the patient, the IMD is configured to deliver spinal cord stimulation (SCS) therapy to reduce pain experienced by the patient,
wherein to generate the patient data that relates to the at least one of the efficacy or the side effect of the therapy, the at least one device is configured to generate data that relates to at least one of patient motion or patient posture over the period of time, and
wherein to analyze the patient data over the period of time, the remote networking device is configured to analyze the data that relates to the at least one of patient motion or patient posture over the period of time with respect to the baseline condition of the patient to identify the change in the at least one of the efficacy or the side effect of the therapy over the period of time.

15. The system of claim 9,
wherein to deliver the therapy to the patient, the IMD is configured to deliver therapy configured to treat urinary incontinence of the patient, and
wherein to generate the patient data that relates to the at least one of the efficacy or the side effect of the therapy, the at least one device is configured to generate data that relates to at least one of urine pressure, urine volume, urine flow, urine pH, temperature, bladder contraction, or urinary sphincter contraction of the patient over the period of time, and
wherein to analyze the patient data over the period of time, the remote networking device is configured to analyze the data that relates to the at least one of urine pressure, urine volume, urine flow, urine pH, temperature, bladder contraction, or urinary sphincter contraction of the patient over the period of time with respect to the baseline condition of the patient to identify the change in the at least one of the efficacy or the side effect of the therapy over the period of time.

16. The system of claim 9,
wherein to deliver the therapy to the patient, the IMD is configured to deliver therapy configured to treat a gastrointestinal disorder of the patient, and
wherein to generate the patient data that relates to the at least one of the efficacy or the side effect of the therapy, the at least one device is configured to generate data that relates to at least one of blood glucose concentration, insulin concentration, core body temperature, distension of a stomach, or pH level of a stomach of the patient over the period of time, and
wherein to analyze the patient data over the period of time, the remote networking device is configured to analyze the data that relates to the at least one of blood glucose concentration, insulin concentration, core body temperature, distension of a stomach, or pH level of a stomach of the patient over the period of time with respect to the baseline condition of the patient to identify the change in the at least one of the efficacy or the side effect of the therapy over the period of time.

17. A remote networking device comprising processing circuitry configured to:
receive patient data transmitted, from an implantable medical device (IMD) system via a network, that relates to at least one of an efficacy or a side effect of a therapy delivered to a patient according to a first therapy program by the IMD system;
analyze the patient data over a period of time with respect to a baseline condition of the patient to identify a change in the at least one of the efficacy or the side effect of the therapy over the period of time;
determine, based on the change in the at least one of the efficacy or the side effect of the therapy over the period of time, a programming change to the first therapy program, wherein the programming change comprises changing from the first therapy program to a second therapy program defining at least one therapy parameter that is different from at least one therapy parameter of the first therapy program;
output, to a user, the programming change to the first therapy program;
receive, from the user, an input indicating approval of the programming change to the first therapy program; and
transmit, to the IMD system via the network, at least one of the programming change or a command to implement the programming change to cause the IMD system to deliver the therapy to the patient according to the second therapy program.

18. The remote networking device of claim 17,
wherein the patient data that relates to the at least one of the efficacy or the side effect of the therapy comprises an activity level of the patient over the period of time, and
wherein to analyze the patient data over the period of time, the processing circuitry is configured to analyze the activity level of the patient over the period of time with respect to the baseline condition of the patient to identify the change in the at least one of the efficacy or the side effect of the therapy over the period of time.

* * * * *